United States Patent [19]

Alvarez et al.

[11] Patent Number: 4,741,900

[45] Date of Patent: * May 3, 1988

[54] ANTIBODY-METAL ION COMPLEXES

[75] Inventors: Vernon L. Alvarez, Morrisville; John D. Rodwell, Yardley, both of Pa.; Chyi Lee, New Brunswick, N.J.; John W. F. Goers, Atascadero, Calif.; Richard C. Siegel, Yorktown Heights, N.Y.; Thomas J. McKearn, New Hope, Pa.

[73] Assignee: Cytogen Corporation, Princeton, N.J.

[*] Notice: The portion of the term of this patent subsequent to Jun. 9, 2004 has been disclaimed.

[21] Appl. No.: 646,328

[22] Filed: Aug. 31, 1984

Related U.S. Application Data

[63] Continuation-in-part of Ser. No. 442,050, Nov. 16, 1982, abandoned, which is a continuation-in-part of Ser. No. 356,315, Mar. 9, 1982, Pat. No. 4,671,958.

[51] Int. Cl.$^4$ .................. A61K 43/00; A61K 49/00; C12Q 1/00; C07K 13/00
[52] U.S. Cl. ........................ 424/85; 424/86; 424/87; 424/1.1; 530/389; 530/390; 530/391; 514/2; 514/6; 435/7; 435/29; 436/548
[58] Field of Search .............. 260/112 R, 112 B; 424/85; 514/2, 6; 435/7, 29; 530/335, 387-391

[56] References Cited

U.S. PATENT DOCUMENTS

| | | | |
|---|---|---|---|
| 3,970,521 | 7/1976 | Zaborsky et al. | 195/63 |
| 4,167,449 | 9/1979 | Gargiulo et al. | 435/16 |
| 4,217,338 | 8/1980 | Quash | 424/1 |
| 4,256,833 | 3/1981 | Ali et al. | 435/7 |
| 4,287,345 | 9/1981 | Kotani et al. | 546/261 |
| 4,331,647 | 5/1982 | Goldenberg | 424/1.1 |
| 4,348,376 | 9/1982 | Goldenberg | 424/1.1 |
| 4,361,544 | 11/1982 | Goldenberg | 424/1.1 |
| 4,419,444 | 12/1983 | Quash | 435/7 |
| 4,421,735 | 12/1983 | Haber et al. | 424/1.1 |
| 4,444,744 | 4/1984 | Goldenberg | 424/1.1 |
| 4,454,106 | 6/1984 | Gansow et al. | 424/1.1 |
| 4,460,559 | 7/1984 | Goldenberg | 424/1.1 |
| 4,460,561 | 7/1984 | Goldenberg | 424/1.1 |
| 4,472,509 | 9/1984 | Gansow et al. | 436/548 |
| 4,479,930 | 10/1984 | Hnatowich | 424/1.1 |

FOREIGN PATENT DOCUMENTS

| | | |
|---|---|---|
| 0038546 | 10/1981 | European Pat. Off. . |
| 3239410A1 | 5/1983 | Fed. Rep. of Germany ........ 424/85 |
| 154520 | 12/1977 | Japan . |
| 155094 | 12/1979 | Japan . |
| 2015530A | 9/1979 | United Kingdom . |

OTHER PUBLICATIONS

March, *Advanced Organic Chemistry*, McGraw Hill Co. N.Y., 1968, 2nd Edition, pp. 817–819.
Bunton, in Oxidation in Organic Chemistry, vol. 1, Widberg, ed., Academic Press, New York, p. 367 (1965).
Carrasquillo et al., Cancer Treatment Rept., 68: 317–328 (1984).
Cooper et al., J. Biol. Chem., 234: 445–448 (1959).
Gansow et al., J. Heterocylic Chem., 18: 297–303 (1981).
Hnatowich et al., Science, 220: 613–615 (1983).
Hnatowich et al., Internat'l J. App. Radiat. Isot., 33: 326–332 (1982).
Kennel et al., Bio. Sci., 34: 150–156 (1984).
Krejcarek and Tucker, Biochem. Biophys. Res. Commun. 77: 581–585 (1977).
Jackson, "Periodic Acid Oxidations" in Organic Reactions, vol. 2, pp. 341–375 (1944).

(List continued on next page.)

*Primary Examiner*—Thomas G. Wiseman
*Assistant Examiner*—Robin Teskin
*Attorney, Agent, or Firm*—Pennie & Edmonds

[57] ABSTRACT

This invention relates to antibody-metal ion complexes having a metal ion coordinately bound to a compatible chelator covalently bound to an antibody or antibody fragment. Also described are methods for intermediates in the preparation of antibody-metal ion complexes. Therapeutic and in vitro and in vivo diagnostic methods utilizing such antibody-metal ion complexes are described.

81 Claims, 4 Drawing Sheets

OTHER PUBLICATIONS

Jentoft and Dearborn, J. Biol. Chem., 254: 4359–4365 (1979).

March, in Advanced Organic Chemistry: Reactions, Mechanisms and Structures; McGraw-Hill Co., N.Y., pp. 824–825 (1978).

Mitral and Lawton, J. Amer. Chem. Soc., 101: 3097–3011 (1979).

Murayama et al., Immunochem, 15: 523–528 (1978).

Powe et al., Cancer Drug Delivery, 1: 125–135 (1984).

Scheinberg, Strand and Gansow Science, 215: 1511–1513 (1982).

Scheinberg, Strand and Gansow, in Monoclonal Antibodies in Drug Development, Aug., ed., pp. 159–171 (1982).

Stanworth and Turner, in Handbook of Experimental Immunology, vol. I, 2d Ed., Weir, ed. Blackwell Scientific Publications, London, Chapter 10 (1973).

Vincour, Diagnostic Imaging, Feb., 1984: 56–61 (1984).

Willan et al., FEBS Lett., 80: 133–136 (1977).

Hurwitz et al., 1980, Applied Biochem, 2:25–35.

(A)

(B)

(C)

(D)

(E)

(F)

(G)

(H)

ANTIBODY-METAL ION COMPLEXES

CROSS-REFERENCE TO RELATED APPLICATIONS

This application is a continuation-in-part of application Ser. No. 442,050, filed Nov. 16, 1982 now abandoned which in turn is a continuation-in-part of application Ser. No. 356,315, filed Mar. 9, 1982, now U.S. Pat. No. 4,671,958.

TABLE OF CONTENTS

1. Field of the Invention
2. Background of the Invention
   2.1. Radioimmunoimaging Using Monoclonal Antibodies
   2.2. Attachment of Radiolabels
   2.3. Radioimmunoimages and Localization
   2.4. Radioimmunotherapy
3. Summary of the Invention
4. Brief Description of the Figures
5. Detailed Description of the Invention
   5.1. Antibodies
   5.2. Compatible Chelators
      5.2.1. Compatible Chelators for Carbohydrate Attachment
      5.2.2. Compatible Chelators for Sulfhydryl Attachment
   5.3. Methods of Attachment to Antibodies and Antibody Fragments
      5.3.1. Attachment to Oxidized Carbohydrate Moieties
         5.3.1.1. Chemical Methods of Oxidation
         5.3.1.2. Enzymatic Methods of Oxidation
         5.3.1.3. Preparation of Antibody-Chelator Conjugates
         5.3.1.4. Stabilization of the Antibody-Chelator Conjugates
      5.3.2. Attachment to Sulfhydryl Groups
   5.4. Preparation of Complexes
   5.5. Uses of Antibody-Metal Ion Complexes
      5.5.1. In Vivo Therapeutics
      5.5.2. In Vivo Diagnostics
      5.5.3. In Vitro Diagnostics
6. Examples: Preparation of Antibody-Metal Ion Complexes Via Carbohydrate Attachment
   6.1. Preparation of Compatible Chelators
      6.1.1. Diethylenetriaminepentaacetic Acid Anhydride
      6.1.2. p-Aminoaniline-diethylenetriaminepentaacetic Acid
      6.1.3. α-N-Diethylenetriaminepentaacetic Acid L-Lysine
      6.1.4. Hydrazide-Diethylenetriaminepentaacetic Acid
      6.1.5. Glycyl-Tyrosyl-Lysine-Diethylenetriaminepentaacetic Acid
      6.1.6. Polyethyleneimine-Diethylenetriaminepentaacetic Acid
      6.1.7. Diethylenetriaminepentaacetic Acid Mono[(4-aminophenyl)menthyl] Amide
      6.1.8. L-Lysine Benzyl Ester-Diethylenetriaminepentaacetic Acid
   6.2. Attachment of Chelator to Antibody and Metal Ion
      6.2.1. Formation of Antibody-Chelator Conjugates
      6.2.2. Formation of Antibody-Metal Ion Complexes
7. Examples: Preparation of Antibody-Metal Ion Complexes Via Carbohydrate or sulfhydryl Attachment
   7.1. Hydrazide-Ficoll
   7.2. (4-Iodoacetyl)-Aminobenzoichydrazide-Ficoll
   7.3. 2-Pyridyl Disulfide Hydrazide DTPA
   7.4. 3-Mercaptopropionichydrazide-DTPA-$^{153}$Gd
   7.5. $^{153}$Gd-DTPA-Hydrazide-Thioacetyl-Aminobenzoichydrazide Ficoll-Acetylthio-IgG
   7.6. (4-Iodoacetyl)-Aminobenzoichydrazide-Ficoll-IgG
   7.7. $^{153}$Gd-DPTA-Hydrazide Thioacetyl-Aminobenzoichydrazide Ficoll-IgG
   7.8. Maleimide Hydrazide Ficoll
8. Examples: Imaging Using Radiolabeled Antibody-Metal Ion Complexes
   8.1. Tumor Imaging
   8.2. Renal Transplant Imaging

1. FIELD OF THE INVENTION

The present invention relates to the general area of antibody systems capable of delivering metal ions to target sites in vivo or in vitro. For embodiments in which the metal ions are radioisotopes or another detectible ion, the antibody systems are capable of being identified and/or detected owing to the radioisotope or other detectible ion attached to the antibody. More particularly, the invention is directed to water-soluble antibody-metal ion complexes comprising metal ions attached by coordinate bonding via a compatible chelator to an antibody molecule which substantially retains the immunospecificity and immunoreactivity of the original antibody. The invention also relates to several methods for preparing such antibody-metal ion complexes as well as antibody-chelator conjugates which are useful in preparing such complexes.

The antibody-metal ion complexes of the invention may be used in a variety of in vitro or in vivo applications involving detection or delivery of a labeled antibody or a metal ion, including, but not limited to, immunological assays, imaging of specific tissues and delivery of metal ions and/or radioisotopes to specific tissue sites.

2. BACKGROUND OF THE INVENTION

A number of agents have been utilized as carrier molecules with limited success in imaging systems. In practice the carrier should be non-toxic and target site specific. Ideally there should be a mechanism for maintenance of the detectable compound or agent at the target site.

Radiopharmaceutical techniques currently used in non-invasive in vivo imaging methods are based upon the ability of the target organ to remove the radiopharmaceutical label from the circulation. These techniques utilize various substances to deliver radioactive compounds to desired target; such substances include substrates, substrate analogs, ligands, hormones, radionuclides, bifunction al chelate (linker groups containing a chelator at one end which is able to bind a heavy metal or radioisotope and a reactive group at the other end which can covalently attach to a target cell) and liposomes (Eckelman and Levanson, 1977, Intl. J. Appl. Radiat. Isot. 28: 67–82).

Other non-invasive techniques currently available are emission tomography, nuclear magnetic resonance imaging, and in vitro spectroscopy. A method employing isothiocyanate as a coupling agent has been used to attach fluorescent compounds to antibody molecules for use in fluorescence microscopy (Brandtzaeg, 1973, Scand. J. Immunol. 2: 273-290).

2.1. RADIOIMMUNOIMAGING USING MONOCLONAL ANTIBODIES

Monoclonal antibodies produced by the hybridoma technique of Köhler and Milstein (1975, Nature 256: 495-497; 1976, Eur. J. Immunol. 6: 511-519) or related techniques provide distinct advantages for use as carriers for imaging systems. First, monoclonal antibodies bind to only one molecular site (i.e., an epitope) with specific binding constants. Second, such antibodies are homogeneous and thus are purified with relative ease. Third, monoclonal antibodies can be made in large quantities by particular hybridoma cell lines.

The discovery of tumor-produced or tumor-associated antigens has allowed the preparation of monoclonal antibodies which are immune-specific for solid tumors such as human colon, breast, heptatoma, melanoma and germ cell tumors (see reviews by Carrasquillo, et al., 1984, Cancer Treatment Repts. 68: 317-328; Kennel, et al., 1984, Bio. Sci. 34: 150-156). Methods have been developed for detecting and locating tumors utilizing antibodies or antibody fragments specific for a variety of categories of tumor-associated antigens, including: oncofetal antigens, placental antigens, oncogenic or tumor virus-associated antigens tissue-associated antigens, organ-associated antigens, ecotopic hormones, normal antigens and variants thereof. For example, Goldenberg, et al. have demonstrated clinical detection of tumors in human patients using $^{131}$I-radiolabeled antibody specific for carcinoembryonic antigen (1978, New Eng. J. Med. 298: 1384-1388; see also disclosures in U.S. Pat. No. 4,331,647 issued to Goldenberg, U.S. Pat. No. 3,927,193 to Hansen, et al.). The methods utilized by Goldenberg, et al., however, required either repeated injection of other radioactive materials or single injection of mixtures of radioactive antibody in order to attain sufficient resolution to distinguish tumors from non-target areas.

The development of monoclonal antibodies specific for myosin, a contractile proteinaceous substance that is accessible to circulating antibody upon cardiac cell death or damage, has allowed development of methods utilizing radioimmunoimaging to locate and quantify myocardial infarcts (see U.S. Pat. 4,036,945 to Haber). Strauss (1984, Diagnostic Imaging Feb. 1984, p. 54) highlights possible uses and potential problems with such antibodies.

2.2 Attachment of Radiolabels

A number of radioisotopes including $^{125}$Iodine, $^{131}$Iodine, $^{111}$Indium, and $^{67}$Copper have been attached to monoclonal or polyclonal antibodies for use in detection of tumors in vivo in animal models. Vincour (1984, Diagnostic Imaging, Feb. 1984, pp. 56-61) reviews the problems experienced with such radiolabeled antibodies, noting especially the need for development of radiolabels which remain more stably affixed to the antibody molecule (Id. at 57).

Recently Hnatowich, et al. (1983, Science 220: 613-615) and Powe, et al. (1984, Cancer Drug Delivery 1: 125-135) described a method of attaching $^{111}$In to antibody molecules or fragments utilizing the water-soluble cylic or bicyclic anhydride of diethylenetriaminepentaacetic acid (DTPA). In both these references the antibody was attached to the water-soluble chelator, DTPA, via an acylation reaction.

2.3. Radioimmunoimages and Localization

A common feature of prior art in vivo images generated either with radioactive metal chelates or $^{131}$Iodine attached to antibodies is non-targeted localization in organs such as liver or spleen (or thyroid for $^{131}$I). Such non-specific localization results in images which do not accurately delineate the position, orientation or size of the intended target. Frequently, "background subtraction" of non-specifically localized radioactivity does not adequately compensate.

2.4. Radioimmunotherapy

The primary distinctions between the materials used in radioimmunoimaging and radioimmunotherapy are the amount and type the radiation employed. In a therapeutic context, radiation is employed to kill target cells while causing minimal toxicity to non-targeted cells. Thus, the radiation ideally has high energy and a short travel range in tissue. Since therapeutic applications involve antibody conjugates are lethal to cells, any non-specific localization presents a serious problem for which one cannot compensate by "background subtraction". Consequently, products and methods which provide limited success with in vivo imaging may not be suitable at all for therapeutic applications.

3. SUMMARY OF THE INVENTION

According to the general methods of the present invention, a metal ion is attached to an antibody or antibody fragment directed against a target antigen. Attachment is accomplished using chelators (i.e., compounds that are able to donate electrons and combine by coordinate bonding with a metal ion to form structures termed chelates or chelation complexes) between the metal ion and the antibody. After formation of antibody-metal ion complexes, non-specifically attached metal ions should be removed. According to the preferred embodiment of the present invention then, removal of non-specifically attached metal ions from the complexes is accomplished using a high performance liquid molecular sieve chromatography system. This enhances the precision and resolution of the radioimages obtained when using the complexes in vivo, and represents a significant improvement over prior methods in which less than 50% of the metal ion may be specifically bound to the chelator portion of the antibody-chelator conjugate, and in which some of the antibody may be aggregated.

In its most general concept, the invention contemplates site selective attachment of compatible chelators to those areas of antibodies or antibody fragments which are not a part of nor directly involved with the antigenic site of the molecule. Thus, after selective attachment of a compatible chelator to one of these sites (located outside the antigen binding region), the antibody conjugate formed has substantially the same immunoreactivity and immunospecificity as the unconjugated antibody or antibody fragment.

In one embodiment of the present invention, compatible chelators containing an amine group selected from the group consisting of primary amine, hydrazine, hydrazide, hydroxylamine, phenylhydrazine, semicarbazide and thiosemicarbazide groups are attached directly to the oxidized carbohydrate moieties of the antibodies or antibody fragments according to methods of attachment described herein.

In another embodiment of the present invention, compatible chelators having certain reactive groups capable of reaction with a sulfhydryl group may be attached to reduced antibodies or reduced (Fab')₂ fragments. Copending application of Siegel, Lee, Alvarez, Rodwell and McKearn, U.S. Ser. No. 646,327, filed on even date herewith is directed specifically to such embodiments, and is incorporated herein by reference.

4. BRIEF DESCRIPTION OF THE FIGURES

The invention may be more fully understood by reference to the appended drawings in which:

FIG. 1 schematically represents the elution pattern of $^{111}$Indium-CYT-015-p-aminoanilinediethylene-triaminepentaacetic acid ($^{111}$In-CYT-015-ADTPA) on high pressure liquid gel permeation chromatography (see Section 6.2.2).

FIG. 2 represents autoradiographic images of Brown Norway (BN) tumor-bearing nude mice injected with $^{111}$Indium-labeled anti-Brown Norway (BN) major histocompatibility complex (MHC) antibody-metal ion complex, $^{111}$In-CYT-015-ADTPA. Images A, B, C and D were taken 24, 24, 48 and 72 hours after injection, respectively (see Section 8.1).

FIG. 3 presents autoradiographic images of control BN tumor-bearing nude mice injected with $^{111}$Indium-labeled anti-human MHC antibody-metal ion complex, $^{111}$In-CYT-012-ADTPA. Images E and F were taken 24 and 72 hours after injection, respectively (see Section 8.1).

5. DETAILED DESCRIPTION OF THE INVENTION

Figure 1:
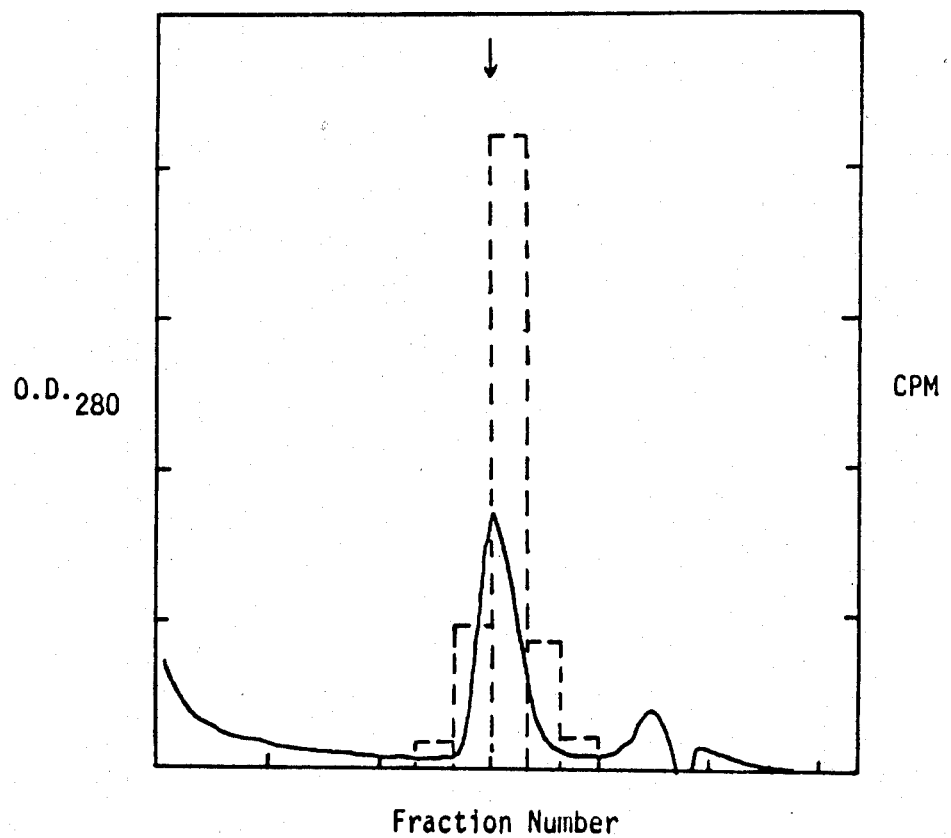

The instant invention concerns antibody-metal ion complexes prepared by attaching a metal ion to an antibody or antibody fragment directed against a target antigen. Compatible chelators capable of coordinate bonding with a metal ion are utilized to attach the metal ions to the antibody or antibody fragment. Such chelators are selectively attached to those areas of antibodies or antibody fragments which are not a part of nor directly involved with the antigenic site of the molecule.

In particular, the invention concerns methods for preparing antibody-metal ion complexes, comprising:

(a) reacting an antibody or antibody fragment with an oxidizing agent to form an aldehyde group in the carbohydrate moiety of the antibody or antibody fragment;

(b) reacting the aldehyde group of the resultant oxidized antibody or antibody fragment with a compatible chelator containing an amine group selected from the group consisting of primary amine, hydrazine, hydrazide, hydroxylamine, phenylhydrazine, semicarbazide and thiosemicarbazide groups to form an antibody-chelator conjugate having substantially the same immunoreactivity and immunospecificity as the unconjugated antibody or antibody fragment; and (c) combining the antibody-chelator conjugate with a metal ion under conditions which allow chelation of the metal ion to the chelator of the antibody-chelator conjugate to form an antibody-metal ion complex.

In certain circumstances, it may be desirable to separate the above-described method for preparing antibody-metal ion complexes into two parts. The first part would produce an antibody-chelator conjugate, which may be considered an intermediate in the production of the final antibody-metal ion complex. Such antibody-chelator conjugates may be stored for later combination with the particular metal ion of interest. Thus, the first part of the two part method would involve steps (a) and (b) above to form the intermediate antibody-chelator conjugate. The second part, possibly at a later point in time, would involve complexing the antibody-chelator conjugate with a metal ion to produce the final antibody-metal ion complex.

Such antibody-metal ion complexes can also be made by alternate methods, as, for example, by first coordinately bonding the compatible chelator to the metal ion, and then reacting the antibody or antibody fragment with the chelator-metal ion complex to form the antibody-metal ion complex. Thus, the invention further includes a method for preparing an antibody-metal ion complex, comprising:

(a) reacting an antibody or antibody fragment with an oxidizing agent to form an aldehyde group in the carbohydrate moiety of the antibody or antibody fragment; and (b) reacting the aldehyde group of the resultant oxidized antibody or antibody fragment with a chelator-metal ion complex, said chelator-metal ion complex comprising a compatible chelator containing an amine group selected from the group consisting of primary amine, hydrazine, hydrazide, hydroxylamine, phenylhydrazine, semicarbazide and thiosemicarbazide groups coordinately bound to a metal ion, to form an antibody-metal ion complex having substantially the same immunoreactivity and immunospecificity as the unconjugated antibody or antibody fragment.

In this embodiment, the compatible chelator is coordinately bound to the metal ion prior to covalent attachment of the chelator to the antibody or antibody fragment.

The invention is also directed to intermediates and final products of the above-described methods. More specifically, this invention is directed to antibody-chelator conjugates comprising a compatible chelator attached through a covalent bond to a carbohydrate moiety of an oxidized antibody or antibody fragment, said antibody-chelator conjugate having substantially the same immunoreactivity and immunospecificity as the unconjugated antibody or antibody fragment. Additionally, the invention concerns antibody-metal ion complexes comprising an antibody-chelator conjugate comprising a compatible chelator attached through a covalent bond to a carbohydrate moiety of an oxidized antibody or antibody fragment, said antibody-chelator conjugate coordinately bound through said compatible chelator to a metal ion to form an antibody-metal ion complex having substantially the same immunoreactivity and immunospecificity as the unconjugated antibody or antibody fragment.

Also encompassed by the invention are antibody-chelator conjugates and antibody-metal ion complexes in which the compatible chelator is attached to a sulfur atom of a reduced antibody or Fab' fragment. These embodiments of the invention involve a method for preparing an antibody-metal ion complex, comprising:

(a) reacting an antibody or the (Fab')$_2$ fragment of an antibody with a mild reducing agent to form a reduced antibody or Fab' fragment having a sulfhydryl group;

(b) reacting said sulfhydryl group with a compatible chelator containing a reactive group selected from the group consisting of haloalkyl groups, p-mercuribenzoate groups, and groups capable of Michael-type addition reactions, to form an antibody-chelator conjugate having substantially the same immunoreactivity and immunospecificity as the unconjugated antibody or (Fab')$_2$ fragment; and (c) combining the antibody-chelator conjugate with a metal ion under conditions which allow chelation of the metal ion to the antibody-chelator conjugate to form an antibody-metal ion complex.

Alternatively, the same antibody-metal ion complexes can be made by another method, comprising:

(a) reacting an antibody or the (Fab')$_2$ fragment of an antibody with a mild reducing agent to form a reduced antibody or Fab' fragment having a sulfhydryl group; and (b) reacting said sulfhydryl group with a chelator-metal ion complex containing a reactive group selected from the group consisting of haloalkyl groups, p-mercuribenzoate groups, and groups capable of Michael-type addition reactions, said chelator-metal ion complex comprising a compatible chelator coordinately bound to a meta ion to, form an antibody-metal ion complex having substantially the same immunoreactivity and immunospecificity as the unconjugated antibody or (Fab')$_2$ fragment.

The product antibody-metal ion complex comprises an antibody-chelator conjugate comprising a compatible chelator attached through a covalent bond to a sulfur atom of a reduced antibody or Fab' fragment, said antibody-chelator conjugate coordinately bound through chelator to a metal ion to form an antibody-metal ion complex having substantially the same immunoreactivity and immunospecificity as the unconjugated antibody or (Fab')$_2$ fragment.

Furthermore, the invention contemplates the intermediate antibody-chelator conjugate which comprises a compatible chelator attached through a covalent bond to a sulfur atom of a reduced antibody or Fab' fragment, said antibody-chelator conjugate having substantially the same immunoreactivity and immunospecificity as the unconjugated antibody or (Fab')$_2$ fragment.

Independent of the method by which the antibody-meta ion complexes of the invention are made, it has been found that improved results may be obtained in ensuing uses of the complexes, particularly in vivo, when the complexes are purified to separate the antibody-metal ion complexes from non-chelated metal ions to obtain antibody-metal ion complexes substantially free of non-chelated metal ions. By "substantially free" of non-chelated metal ions is meant at least about 80–90 percent free of such ions. More specifically, the purified complexes of the invention contain metal ion chelated to the chelator, but are substantially free of metal ion adventitiously bound to antibody, that is, metal ion associated with the antibody protein or carbohydrate and not complexed to the chelator. The purification can be accomplished by any suitable purification method, including but not limited to high performance gel permeation liquid chrom;atography.

This purification step has the additional benefit of removing undesirable aggregates of antibodies prior to administration. Any such antibody aggregates or denatured antibodies would be taken up by the reticuloendothelial system for removal, and this transport away from the target site or specific tissue to be imaged would diminish the degree of localization or the quality of the image.

The antibody-metal ion complexes of the invention are ideally suited for high-resolution tissue imaging in vivo. Such imaging of specific tissue involves administering to a human an effective amount of an antibody-metal ion complex, wherein said antibody-metal ion complex is immunoreactive with and immunospecific for an antigenic determinant of said specific tissue and substantially non-immunoreactive with and non-immunospecific for non-specific tissue and said antigenic determinant is not found in substantial amount in non-specific tissue. As demonstrated in the examples hereafter, this method can be used to localize specific tissue with a minimum of "background" dispersal of metal ion.

Further in vivo uses of the antibody-metal ion complexes of the invention include therapeutic treatment of cellular disorders. Such methods comprise administering a therapeutically effective amount of an antibody-metal ion complex of the invention, said antibody-metal ion complex being immunoreactive with and immunospecific for a target site associated with said cellular disorder and substantially non-immunoreactive with and non-immunospecific for tissue not associated with said cellular disorder, and wherein the metal ion emits cytotoxic beta particles or alpha particles.

Finally, the complexes of the invention may also be used in methods for testing for antigen, which involve, for example, (a) mixing an antibody-metal ion complex with a sample suspected of containing a particular antigen, the antibody-metal ion complex being immunoreactive with and immunospecific for said antigen, and (b) detecting any interaction of said antibody-metal ion complex with any antigen in the sample.

Other applications for in vitro uses may similarly be found and developed by one of ordinary skill.

5.1. Antibodies

According to the present invention, antibodies directed against any antigen or hapten may be used. Although conventional antibodies (antisera) may be used, monoclonal antibodies offer several advantages. Each monoclonal antibody is specific for one antigenic determinant. Additionally, large amounts of each monoclonal antibody can be produced.

Antibodies used in the present invention may be directed against any target, e.g., tumor, bacterial, fungal, viral, parasitic, mycoplasmal, histocompatability, differentiation and other cell membrane antigens, pathogen surface antigens, toxins, enzymes, allergens, drugs and any biologically active molecules.

Drugs of particular interest are opioids, amphetamines, barbiturates, steroids, catecholamines, dilantin, theophylline, histamine, cannabinoids, and the like. For a more complete list of antigens, see U.S. Pat. No. 4,193,983, particularly columns 7–11, which patent specification is incorporated herein by reference. When it is desired to image cardiovascular disease or damage following, e.g., myocardial infarcts, antibodies directed against myosin or another cardiac cytosol protein may be used. Additionally, a combination of antibodies reactive to different antigenic determinants may be used. Immunoglobulins which may be used as carriers include: certain classesof antibodies such as IgA, IgD, IgE, IgM; certain classes of IgG; or certain fragments of immunoglobulins, e.g., half antibody molecules (a single heavy:light chain pair), or Fab, Fab', or (Fab')$_2$ fragments.

Use of antibody fragments may be advantageous for tissue imaging systems because these antibody fragments permeate target sites at an increased rate. The Fab' fragments of IgG immunoglobulins are obtained by cleaving the antibody molecule with pepsin (resulting in a bivalent fragment, (Fab')$_2$) or with papain (resulting in 2 univalent fragments, 2 Fab). Parham, 1983, J. Immunol. 131: 2895-2902; Lamoyi and Nisonoff, 1983, J. Immunol. Meth. 56: 235-243. The bivalent (Fab')$_2$ fragment can be split by mild reduction of one or a few disulfide bonds to yield univalent Fab' fragments. The Fab and (Fab')$_2$ fragments are smaller than a whole antibody molecule and, therefore, permeate the target site or tissue more easily. This may offer an advantage for in vivo imaging since conjugates will more readily penetrate in vivo sites (e.g., tumor masses, infection sites, etc.). An additional advantage is obtained when using conjugates formed with antibody fragments because these fragments do not cross a placental barrier. As a result, using this embodiment of the invention, an in vivo site (such as a tumor) may be imaged in a pregnant female without exposing the fetus to the imaging compound.

5.2. COMPATIBLE CHELATORS

As used herein, the term "compatible chelator" means any compound that (a) is able to donate electrons and combine by coordinate bonding with a metal ion to form structures called chelates or chelation complexes and (b) is suitable for attachment to an antibody or antibody fragment without loss of ability to chelate metal ions or destruction of the immunoreactivity or immunospecificity of the antibody or antibody fragment. Where necessary, derivatives of known chelators may be synthesized such that the product is a compatible chelator suitable for attachment to antibodies or antibody fragments by methods of the invention.

Of additional interest are compatible chelators which have multiple sites for chelation of metal ions. For multiple site compatible chelators, a single covalent attachment to an antibody or antibody fragment would result in a conjugate capable of binding metal ion at a number of sites. Radioactive complexes of such conjugates would have high specific radioactivity, that is, high radioactivity per antibody molecule.

Alternatively, higher specific radioactivity (or higher ratios of metal ion to antibody molecule) can be achieved by attachment of a single site compatible chelator at a plurality of sites of the antibody or antibody fragment. This plurality of sites may be introduced into the antibody or antibody fragment by either of two methods. Firt, one may generate multiple aldehyde groups and/or sulfhydryl groups in the same antibody molecule. Second, one may attach to aldehyde or sulfhydryl of the antibody molecule a "branched linker" having multiple functional sites for subsequent attachment to compatible chelators. The functional sites of the branched linker may be aldehyde or sulfhydryl groups, or may be any chemical site to which compatible chelators may be attached. Still higher specific radioactivities may be obtained by combining these two approaches, that is, attaching multiple site compatible chelators at several sites on the antibody or antibody fragment.

Immediately below are identified some important classes of compatible chelators suitable for use in the present inventions. Compatible chelators include, but are not limited to, derivatives of diethylenetriaminepentaacetic acid, ethylenediaminetetraacetic acid (EDTA), dimercaptosuccinic acid, 2,3-dimercaptopropanesulfonic acid, metallothioein and cryptates, such as those recently described by Gansow, et al. (1981, J. Heterocyclic Chem. 18: 297).

5.2.1. COMPATIBLE CHELATORS FOR CARBOHYDRATE ATTACHMENT

As previously explained, compatible chelators are utilized to attach metal ions to antibody molecules. According to the present invention, suitable compatible chelators for reaction with oxidized antibodies or oxidized antibody fragments include those containing an amine selected from the group consisting of primary amine, hydrazine, hydrazide, hydroxylamine, phenylhydrazine, semicarbazide and thiosemicarbazide groups.

Such reactive functional groups may exist as part of the structure of the chelator, or may be introduced by suitable chemistry on chelators not containing such groups.

For example, diethylenetriaminepentaacetic acid (DTPA) lacks the appropriate amine group for facile attachment to oxidized carbohydrate. However, chemical modification can produce a variety of suitable derivatives, such as amine-containing derivatives of mixed anhydrides of DTPA including, but not limited to p-aminoaniline-DTPA, hydrazide-DTPA, phenylhydrazide-DTPA, hydroxylamine-DTPA, semicarbazide-DTPA, thiosemicarbazide-DTPA, polyethyleneimine-DTPA, p-phenylenediamine-DTPA, DTPA mono[(4-aminophenyl)methyl amide and amino acid-containing derivatives of DTPA, including, but not limited to α-N-DTPA-L-lysine, glycyl-tyrosyl-lysine-DTPA and L-lysine benzyl ester-DTPA.

5.2.2. COMPATIBLE CHELATORS FOR SULFHYDRYL ATTACHMENT

According to the present invention, suitable compatible chelators for attachment to reduced antibody or antibody fragments include chelators having certain reactive groups capable of reaction with a sulfhydryl group of a reduced antibody or Fab' fragment. Such reactive groups include, but are not limited to, reactive haloalkyl groups (including, for example, haloacetyl groups), p-mercuribenzoate groups and groups capable of Michael-type addition reactions (including, for example, maleimides and groups of the type described in Mitra and Lawton, 1979, J. Amer, Chem. Soc. 101: 3097-3110). By the term "haloalkyl" is meant any alkyl group of one to three carbon atoms substituted with bromine, iodine or chlorine. Iodoalkyl groups, for example, may be introduced into the structure of known chelators, including, but not limited to, diethylenetriaminepentaacetic acid, ethylenediaminetetraacetic acid, dimercaptosuccinic acid, 2,3-dimercaptopropanesulfonic acid, metallothioein and cryptates.

5.3. METHODS OF ATTACHMENT TO ANTIBODIES AND ANTIBODY FRAGMENTS

According to the methods of the present invention, a compatible chelator (or compatible chelator-metal ion complex) is attached to an antibody directed against a target antigen, by (a) attachment to the carbohydrate moieties of the antibody or antibody fragment, or (b) attachment to sulfhydryl groups of the antibody molecule. Whichever method is used, the attachment must not significantly change the essential characteristics of the antibody or antibody fragment, such as immunospecificity and immunoreactivity. Additional considerations include simplicity of reaction and stability of the antibody conjugate produced.

5.3.1. ATTACHMENT TO OXIDIZED CARBOHYDRATE MOIETIES

Glycoproteins are biologically important macromolecules which share structural characteristics including carbohydrate residues covalently attached to a polypeptide backbone. Since antibodies are glycoproteins, compounds may be attached to the carbohydrate moiety of the molecule. Some of the carbohydrate moieties are located on the Fc region of the immunoglobulin and are required in order for C1 binding to occur. The carbohydrate moiety of the Fc region of an immunoglobulin may be utilized in the scheme described herein. Alternatively, the Fab or Fab' fragments of any immunoglobulins which contain carbohydrate moieties may be utilized in the reaction scheme described herein. An example of such an immunoglobulin is the human IgM sequenced by Putnam, et al. (1973, Science 182: 287).

As explained in detail below, the carbohydrate side chains of antibodies or Fab or Fab' fragments may be selectively oxidized to generate aldehydes. The resulting aldehydes may then be reacted with amine groups (e.g., ammonia derivatives such as a primary amine, hydroxylamine, hydrazine, hydrazide, phenylhydrazine, semicarbazide or thiosemicarbazide) to form a Schiff base or reduced Schiff base (e.g., imine, oxime, hydrazone, phenylhydrazone, semicarbazone or thiosemicarbazone, or reduced forms thereof).

Alternatively, the carbohydrate moiety of the antibody may be modified by enzymatic techniques so as to enable attachment to or reaction with other chemical groups. One example of such an enzyme is galactose oxidase which oxidizes galactose in the presence of oxygen to form an aldehyde.

5.3.1.1. CHEMICAL METHODS OF OXIDATION

Oxidation of the carbohydrate portion or moiety of antibody molecules leads to formation of aldehyde groups. A variety of oxidizing agents can be used, such as periodic acid, paraperiodic acid, sodium metaperiodate and potassum metaperiodate. Among these, oxygen acids and salts thereof are preferred since secondary or undesirable side reactions are less frequent. For a general discussion, see Jackson, 1944, *Organic Reactions* 2, p. 341; Bunton, 1965, *Oxidation in Organic Chemistry*, Vol. 1 (Wiberg, ed.), Academic Press, New York, p. 367.

Oxidation of antibodies with these oxidizing agents can be carried out by known methods. In the oxidation, the antibody is used generally in the form of an aqueous solution, the concentration being generally less than 100 mg/ml, preferably 1 to 20 mg/ml. When an oxygen acid or a salt thereof is used as the oxidizing agent, it is used generally in the form of an aqueous solution, and the concentration is generally 0.001 to 10mM and preferably 1.0 to 10mM. The amount of the oxygen acid or salt thereof depends on the kind of antibody, but generally it is used in excess, for example, twice to ten times as much as the amount of the oxidizable carbohydrate. The optimal amount, however, can be determined by routine experimentation.

In the process for oxidizing antibodies with oxygen acids or salts thereof, the optional ranges include a pH of from about 4 to 8, a temperature of from 0° to 37° C., and a reaction period of from about 15 minutes to 12 hours.

During the oxidation of the glycoprotein with an oxygen acid or a salt thereof, light is preferably excluded to prevent over-oxidation of the glycoprotein.

5.3.1.2. ENZYMATIC METHODS OF OXIDATION

Oxidation of the carbohydrate portion of antibody molecules may also be done with the enzyme, galactose oxidase [Cooper, et al., 1959, J. Biol. Chem. 234: 445–448]. The antibody is used in aqueous solution, the concentration being generally 0.5 to 20 mg/ml. The enzyme generally is used at about 5 to 100 units per ml of solution, at a pH ranging from about 5.5 to about 8.0. The influence of pH, substrate concentration, buffers and buffer concentrations on enzyme reaction are reported in Cooper, et al., supra.

5.3.1.3. PREPARATION OF ANTIBODY-CHELATOR CONJUGATES

The antibody-chelator conjugates (or antibody-metal ion complexes when pre-chelated metal ion is attached to the chelator prior to reaction of the chelator with antibody) of the invention may be produced by reacting the oxidized antibody with a compatible chelator having an available amine group selected from the group consisting of primary amine, hydrazine, hydrazide, hydroxylamine, phenylhydrazine, semicarbazide and thiosemicarbazide groups. The immediately resulting products (antibody-chelator conjugates or antibody-metal ion complexes) contain a carbon-nitrogen double bond resulting from elimination of a molecule of water from the initial addition products:

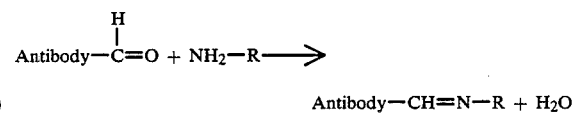

For a general discussion of the reaction of aldehydes with hydrazides, see March, 1978, *Advanced Organic Chemistry: Reactions, Mechanisms and Structure*, McGraw-Hill Co., N.Y., pp. 824–825.

A solution of the oxidized antibody at a concentration of from about 0.5 to 20 mg/ml is mixed with the compatible chelator (molar ratios of reactive chelator group to antibody aldehyde ranging from about 1 to about 10,000) and the solution incubated for from about 1 to 18 hours. Suitable temperatures are from 0° to 37° C. and pH may be from about 6 to 8.

5.3.1.4. STABILIZATION OF THE ANTIBODY-CHELATOR CONJUGATES

After the antibody-chelator conjugates (or antibody-metal ion complexes) have been formed between the antibody and a compatible chelator as described in Section 5.3.1.3, they can optionally be stabilized with a suitable reducing agent, such as sodium cyanoborohydride or sodium borohydride:

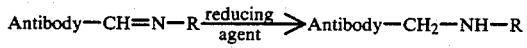

Reducing agent is generally added to a molar excess of from about 10 to 100 fold molar excess over available aldehyde groups. For a general discussion, see Jentoft and Dearborn, 1979, J. Biol. Chem. 254: 4359.

5.3.2. ATTACHMENT TO SULFHYDRYL GROUPS

Free sulfhydryl groups can be generated from the disulfide bonds of the immunoglobulin molecule. This is accomplished by mild reduction of the antibody molecule. The disulfide bonds of IgG which are generally most susceptible to reduction are those that link the two heavy chains. The disulfide bonds located near the antigen binding region of the antibody molecule remain relatively unaffected. Such reduction results in the loss of ability to fix complement but does not interfere with antibody-antigen binding ability (Karush, et al., 1979, Biochem. 18: 2226-2232). The free sulfhydryl groups generated in the intra-heavy chain region can then react with reactive groups of a compatible chelator to form a covalent bond which does not interfere with the antigen binding site of the immunoglobulin. Such reactive groups include, but are not limited to, reactive haloalkyl groups (including, for example, haloacetyl groups), p-mercuribenzoate groups and groups capable of Michael-type addition reactions (including, for example, maleimides and groups of the type described in Mitra and Lawton, 1979, J. Amer, Chem. Soc. 101: 3097-3110). By the term "haloalkyl" is meant any alkyl group of one to three carbon atoms substituted with bromine, iodine or chlorine.

Details of the conditions, methods and materials suitable for mild reduction of antibodies and antibody fragments as described generally herein may be found in Stanworth and Turner, IN Handbook of Experimental Immunology, Vol. 1, Second Edition, Weir (ed.), Chapter 10, Blackwell Scientific Publications, London, 1973, which chapter is incorporated herein by reference.

Antibody-chelator conjugates (or antibody-metal ion complexes when pre-chelated metal ion is attached to the chelator prior to reaction of the chelator with antibody) which are produced by attaching a compatible chelator to a free sulfhydryl group of a reduced immunoglobulin or reduced antibody fragment do not activate complement. Thus, complexes of the conjugates may advantageously be used in in vivo imaging systems where release of the metal ion is not desirable.

5.4. PREPARATION OF COMPLEXES

Chelator-metal ion complexes may be prepared by attaching the metal ion directly to the chelator. Conventional methods of attaching metal ions to chelators may be utilized to accomplish binding to chelator. For example, $^{111}$Indium ($^{111}$In) may be attached to a water-soluble chelator compound by incubation of $^{111}$In-Cl$_3$ in sodium acetate with the chelator, e.g., for 1 hour at 37° C.

As explained previously, according to the present invention, the metal ion may be attached to the chelator either before or after the chelator is attached to the antibody molecule. Whatever method of attachment is utilized, it may be significant for many applications that any metal ion not specifically attached to the chelator compound be removed before the complexes are used, particularly in vivo. According to the preferred embodiment, the non-specifically attached metal ion is removed using a high performance liquid molecular sieve chromatography system.

For in vitro detection systems, e.g., improved immunoradiometric assay systems, the antibody molecule or antibody fragment may be attached to a compatible chelator according to methods described herein, and the antibody-chelator conjugate intermediate may be purified, if necessary, and stored frozen at −20° C. until needed. The metal ion may then be attached to the antibody-chelator conjugate. For instance, $^{111}$Indium may be attached by incubation of $^{111}$InCl$_3$ with the antibody-chelator conjugate in acetate buffer, pH 6.0, at 37° C. for 1 hour. Such method of attachment advantageously allows purification of the antibody-chelator intermediate without exposing the preparer to excessive handling of radioactive materials, and without necessity of lengthy storage of radioisotopes in the work areas.

5.5. USES OF ANTIBODY-METAL ION COMPLEXES

The antibody-metal ion complexes of the invention are useful in a variety of therapeutic and in vitro and in vivo diagnostic applications.

Throughout this application the term "cellular disorder" is meant to include all neoplasms, including cancers, adenomas, and hyperplasias; certain immunological disorders, including autoimmune diseases, diseases (e.g., after bone marrow graft-versus-host transplantation), immune suppressive diseases, e.g., after kidney or bone marrow transplantation. Treatment of such cellular disorders involving, for example, bone marrow transplantation, may include purging (by killing) undesired cells, e.g., malignant cells or mature T lymphocytes.

5.5.1. IN VIVO THERAPEUTICS

Therapeutic applications center generally on treatment of various cellular disorders, including those broadly described above, by administering an effective amount of the antibody-metal ion complexes of the invention. The properties of the antibody in being immunospecific for and immunoreactive with a particular antigen render it ideally suited for delivering metal ions to specific cells, tissues, organs or any other site having that particular antigen.

According to this aspect of the invention, the antibody or antibody fragment of the antibody-metal ion complex functions to deliver the complex to the target site, at which site the metal ion, which is chosen for its cell killing properties, is able to destroy nearby cells. Suitable beta emitting ions for therapeutic uses include: $^{46}$Scandium, $^{47}$Scandium, $^{48}$Scandium, $^{72}$Gallium and $^{73}$Gallium. Suitable alpha emitting metal ions include those with a relatively short half-life of about four days or less, including $^{211}$Bismuth, $^{212}$Bismuth $^{213}$Bismuth and $^{214}$Bismuth, with $^{212}$Bismuth being preferred.

In vivo administration may involve use of pharmaceutical compositions of antibody-metal ion complex in any suitable carrier, including serum or physiological saline, with or without another protein, such as human serum albumin. Dosage of the complexes may readily be determined by one of ordinary skill, and may differ depending upon the nature of the cellular disorder and the metal ion used. Route of administration may be parenteral, with intravenous administration generally preferred.

5.5.2. IN VIVO DIAGNOSTICS

In vivo diagnostic applications involve imaging of specific tissues or cellular disorders by administration of a sufficient amount of the antibody-metal ion complexes of the invention to enable the complexes to localize at the tissue in the appropriate time frame. Dosage and other aspects of administration of the complexes in vivo are generally discussed in the preceding section.

A wide variety of metal ions suitable for in vivo tissue imaging have been tested and utilized clinically. For imaging with radioisotopes the following characteristics are generally recognized as desirable and/or necessary: (a) low radiation dose to the patient; (b) high photon yield which permits a nuclear medicine procedure to be performed in a short time period; (c) ability to be produced in sufficient quanitites; (d) acceptable cost; (e) simple preparation for administration; and (f) no requirement for subsequent isolation of the patient. These characteristics generally translate into the following: (a) the radiation exposure to the most critical organ is less than 5 rad; (b) a single image can be otained in several hours; (c) the radioisotope does not decay by emission of a particle (e.g., $\beta^-$ or $\beta^+$); (d) the isotope can be readily detected; and (e) the half-life is less than four days. (Lamb and Kramer, "Commercial Production of Radioisotopes for Nuclear Medicine", IN Radiotracers For Medical Applications, Vol. 1, Rayudu (ed.), CRC Press, Inc., Boca Raton, pp. 17-62.)

An alternative method for imaging with radioisotopes involves positron emission tomography. Suitable positron emitting isotopes include $^{43}$Scandium, $^{44}$Scandium, $^{52}$Iron, $^{55}$Cobalt and $^{68}$Gallium Tissue imaging may also utilize nonradioactive paramagnetic metal ions such as $^{54}$Iron, $^{56}$Iron, $^{57}$Iron $^{58}$Iron $^{157}$Gadolinium and $^{55}$Manganese, which are detectible by nuclear magnetic resonance spectroscopy.

Tissues which one may image include any solid neoplasm, certain organs such as lymph nodes, parathyroids, spleen and kidney, sites of inflammation or infection (e.g., macrophages at such sites), myocardial infarction or thromboses (neoantigenic determinants on fibrin or platelets), etc.

5.5.3. IN VITRO DIAGNOSTICS

In vitro analytical procedures for detecting a particular antigen using the antibody-metal ion complexes of the invention employ standard immunoradiometric assay techniques. For a general review of such techniques, see Hales and Woodhead, Methods in Enzymology 70: 334–355 (1980). Generally, immunoradiometric assays (IRA) involve labeled antibodies to detect unlabeled antigens. Numerous variations of the immunoradiometric assay have been developed, including for example, the two-site IRA and the indirect IRA. These two methods are discussed generally below.

The objective of the two-site IRA is to use a specific antibody on a solid phase, e.g., cellulose or Sepharose, to extract antigen. While the antibody remains bound to the solid phase, a second labeled antibody is bound to another site on the antigen. The second antigen can then be measured as a function of the amount of bound labeled antibody. In this method the antigen is bound to two different antibodies at two sites on the antigen. In another method purified antigen is adsorbed or coupled to a solid phase support.

In the indirect IRA the (first) antibody used for measuring antigen is indirectly labeled through the use of a labeled antibody to the immunoglobulin of the same species as that in which the first antibody is raised. This labeled anti-immunoglobulin antibody is then reacted with the first antibody and antigen. The labeled antibody can also be used in the conventional or two site IRAs.

These diagnostic techniques and others are intended to be encompassed by the present invention.

In the context of this invention, all of these IRA methods for testing for antigen have in common the following two steps: (a) mixing an antibody-metal ion complex with a sample suspected of containing the antigen, and (b) detecting the interaction, if any antigen is present, of said complex with the antigen.

For in vitro diagnostics, all of the gamma and positron emitting metal ions, as well as the paramagnetic metal ions in Section 5.5.2, as well as 153Gadolinium are suitable. For fluorescence diagnostic assays, lanthanides may be employed, including Praseodymium, Neodymium, Samarium, Europium, Gadolinium, Terbium, Dysprosium, Holmium, Erbium, Thulium and Ytterbium.

EXAMPLES

Preparation of Antibody-Metal Ion Complexes via Carbohydrate Attachment

The following experiments demonstrate the formation of specifically radiolabeled antibody-metal ion complexes which according to the instant inventions are useful for in vivo imaging systems, for in vivo therapy and for in vitro detection systems.

6.1. PREPARATION OF COMPATIBLE CHELATORS

As described above, compatible chelators are utilized to attach a metal ion, such as a radioisotope, to an antibody or antibody fragment. The following examples illustrate preparation of suitable compatible chelators.

In all the following examples the water used as a solvent or to form solvent systems and buffers was first passed through a Chelex ® resin-containing column (BioRad Laboratories, Inc., Richmond, CA) and stored in acid-washed containers.

6.1.1. Diethylenetriaminepentaacetic Acid Anhydride

The mixed anhydride of diethylenetriaminepentaacetic acid (DTPA mixed anhydride) was prepared according to the method described by Krejcarek and Tucker, 1977, Biochem. Biophys. Res. Commun. 77: 581–585. Briefly, 2.54 mmole DTPA and 12.7 mmole triethylamine were dissolved in 20 ml of water and the solution dried under vacuum to yield the DTPA salt. The salt was then dissolved in 20 ml of a solvent system consisting of acetonitrile-dimethylformamide (CH$_3$CN-DMF) in a ratio of 65:35, and cooled to $-5°$ C. in an ice-rock salt bath. After the addition of 2.54 mmole isobutylchloroformate, the solution was stirred under nitrogen for twenty minutes. The DTPA mixed anhydride product which remained in solution could be separated from the precipitated triethylamine hydrochloride either by filtering or by centrifuging and decanting the supernatant.

6.1.2. P-Aminoaniline-Diethylenetriamine-Pentaacetic Acid

P-Aminoaniline-diethylenetriaminepentaacetic acid anhydride (ADTPA) was prepared as follows. Briefly, 25.4 mmole p-phenylenediamine in 50 ml of a solvent system containing $CH_3CN$-DMF (65:35) was added to 2.0 g of fresh DTPA mixed anhydride prepared as described in Section 6.1.1. The solution was maintained with stirring at $-5°$ C. for 2 hours under nitrogen, and then at room temperature (approximately 24° C.) overnight. At the end of this time period, the initially homogeneous solution had become a heterogeneous mixture. This heterogeneous reaction mixture was then evaporated to dryness under vacuum, and the resulting residue dissolved in a small aliquot 50 ml of distilled water. The pH of the reaction mixture was adjusted to 11.0 using sodium hydroxide (NaOH) solution (6M). Unreacted p-phenylenediamine was removed by extraction with methylene chloride. The aqueous phase was collected, concentrated under vacuum and lyophilized to yield a pale white powder of crude ADTPA. The crude ADTPA was purified by elution through a packed silica column using ethanol-aqueous ammonia (4:1), followed by distilled water.

6.1.3. α-N-Diethylenetriaminepentaacetic Acid L-Lysine

α-N-Diethylenetriaminepentaacetic acid L-lysine (KDTPA) was prepared as follows: 2.26 mmole of N-ε-carbobenzoxy-L-lysine benzyl ester (Vega Biochemicals, Tucson, Arizona) was reacted with 2.71 mmole triethylamine in 40 ml of acetonitrile, while maintained with stirring at room temperature for 30 minutes under nitrogen. Then 2.26 mmole of freshly prepared DTPA mixed anhydride in 20 ml $CH_3CN$-DMF (65:35) was added. The reaction mixture was maintained with stirring under nitrogen for 2 hours at 0° C, and then overnight at room temperature. The solution was evaporated to dryness under vacuum and the resulting residue dissolved in 50 ml distilled water. The unreacted lysine ester was removed by adjusting the pH to 11.0 with NaOH solution and extracting with methylene chloride. The aqueous solution was then concentrated under vacuum and the pH adjusted to neutrality with a small aliquot of hydrochloric acid (HCl). The carbobenzoxy protecting group was then removed using palladium-/activated charcoal (5% palladium) under 30 lb-inch$^2$ hydrogen for 4 hours in a Parr Hydrogenator. The resulting mixture was filtered through Celite$^R$, and the filtrate lyophilized to yield a white powder of crude KDTPA. This crude product was further purified to yield KDTPA by elution through a silica gel column with ethanol-aqueous ammonia (4:1), followed by distilled water.

6.1.4. Hydrazide-Diethylenetriameinepenta-Acetic Acid

The hydrazide derivative of DTPA (HDTPA) was prepared as follows: 6.3 mmole of anhydrous hydrazine was dissolved in 2 ml dimethylformamide (DMF) and reacted with 2.54 mmole DTPA mixed anhydride in 20 ml $CH_3CN$-DMF (65:35). The heterogeneous mixture was maintained with stirring at 4° C. for 1 hour, and then at room temperature for 1 hour. The reaction mixture was evaporated to dryness under vacuum, and the residue dissolved in ethanol-aqueous ammonia (4:1). The product was then purified by elution through silica gel with ethanol-aqueous ammonia, followed by distilled water. Product-containing fractions were collected, and the pH adjusted to 3.0 using a small aliquot of hydrochloric acid. The solution was filtered and the filtrate lyophilized to yield HDTPA.

6.1.5. Glycyl-Tyrosyl-Lysine-Diethylene-Triaminipentaacetic Acid

The glycyl-tyrosyl-lysine-diethylenetriaminepentaacetic acid anhydride (GYK-DTPA) was prepared as follows. The initial peptide reactant N-FMOC-glycyl-(o-benzyl-tyrosyl-(ε-N-carbobenzoxy)) lysine was prepared according to standard solid phase synthetic methods described by Baranz and Merrifield, IN The Peptides, Vol. 2, Gross and Meienhoffer (ed.), Acad. Press, New York, pp. 3–385. The derivatized peptide was cleaved from the resin and partially deblocked by bubbling hydrogen bromide (HBr) gas through a suspension of the reaction mixture in trifluoroacetic acid containing methoxybenzene (a fifty-fold molar excess over tyrosine) for 60 minutes at room temperature. The resin was removed by filtration and the filtrate evaporated to dryness. The residue was dissolved in a minimum amount of methanol, and the product precipitated with ether and used without further purification.

One mole N-FMOC-glycyl-tryrosyl-lysine in DMF was reacted with 1 mole DTPA mixed anhydride, prepared as described in Section 6.1.1 except that diisopropylethylamine was used in place of triethylamine, for 30 minutes at $-15°$ C., and then maintained at room temperature for 1 hour. The solvent was removed by rotary evaporation, and the oily residue dissolved in a small aliquot of DMF. Distilled water was added to precipitate the FMOC-GYK-DTPA produced. The FMOC group was removed by addition of an equal volume of 40% dimethylamine to a solution of FMOC-GYK-DTPA in DMF, followed by incubation for 30 minutes at room temperature. The solvent was evaporated to dryness and the residue taken up in distilled water. The crude product was purified by extraction with ethyl acetate, and the resulting aqueous solution of GYK-DTPA was lyophilized to dryness.

6.1.6. Polyethyleneimine-Diethylenetriamine-Pentaacetic Acid polyethyleneimine-diethylenetriaminepentaacetic acid (PEI-DTPA) was prepared as follows: 2.54 mmole DTPA was dissolved in 100 ml $H_2O$, and the pH was adjusted to 5.0 using 6M NaOH solution. Then 12.7 mmole 1-ethyl-3-(3-dimethylaminopropyl) carbodiimide (Sigma Chemical Co., St. Louis, MO) and 144 umole polyethyleneimine (Polysciences, Inc. Warrington, Pa.) were added. The pH was readjusted to 5.0 using aqueous HCl, and the solution was maintained with stirring at room temperature overnight. The PEI-DTPA formed was separated from the reaction mixture either by reverse phase chromatography or by gel filtration.

6.1.7. Diethylenetriaminepentaacetic Acid Mono[(4-Aminophenyl)Methyl Amide

P-Nitrobenzylamine HCl (174 mg, 0.92 mmole) was treated with 3 ml of 0.3 N NaOH to form yellow oil and the oil was extracted with $CH_2Cl_2$. The organic layer was separated and dried in vacuo to obtain the p-nitrobenzylamine free base.

DTPA anhydride (CDTPA) was synthesized according to the procedure of Hnatowich, et al. (1982, Int. J. Appl. Radiat. Isot. 33: 327–332).

A solution of CDTPA (1.64 g, 4.6 mmole in 150 ml of dry dimethylformamide (DMF)) was added to the p-nitrobenzylamine and warmed to 60° C. under $N_2$ gas. After stirring for 24 hours, thin layer chromatography showed no unreacted p-nitrobenzylamine in the solution. The solution was dried in vacuo and hydrolyzed with saturated $NaHCO_3$ solution. The p-nitrobenzylamine-DTPA adduct was separated from the reaction mixture using $C_{18}$ reversed phase high performance liquid chromatography (HPLC). It was then reduced using a Parr Hydrogenator in the presence of 5% palladium/activated charcoal under 30 lbs/in$^2$ $H_2$ gas for 4 hours. The solution was dried by rotary evaporation and the oil was triturated with acetone-ether (4:1) to yield a pale yellow product.

6.1.8. L-Lysine Benzyl Ester-Diethylenetriaminepentaacetic Acid

N-ε-Z-L-Pentaacetic Acid lysine benzyl ester HCl (0.5 g, 1.12 mmole, Viga Chemical Co., Tucson, Ariz.) was adjusted to pH 9.0 with 5% $NaHCO_3$ and 0.1N NaOH solutions. The aqueous solution was extracted with $CH_2Cl_2$ and the organic layer was separated. The organic solution was dried over sodium sulfate and then was filtered, the filtrate evaporated to dryness in vacuo, obtaining the free base form of N-ε-Z-L-lysine benzyl ester.

DTPA anhydride (CDTPA) was synthesized according to the procedure of Hnatowich, et al. (1982, Int. J. Appl. Radiat. Isot. 33: 327–332).

To a solution of 2.19 g (6.15 mmole) of CDTPA in 200 ml of dry dimethylformamide was added the above prepared N-ε-Z-L-lysine benzyl ester free base and warmed to 60° C. under $N_2$ gas for 24 hours. All lysine ester was reacted with CDTPA from thin layer chromatography analysis. The reaction mixture was dried in vacuo and the unreacted anhydride was hydrolyzed with saturated $NaHCO_3$ solution. The N-ε-Z-L-lysine benzyl ester-DTPA adduct was isolated from the mixture using $C_{18}$ reversed phase HPLC. The CBZ protecting group was removed by hydrogenolysis in a Parr Hydrogenator in the presence of 5% palladium/activated charcoal and 30 lbs/in$^2$ $H_2$ gas for 5 hours. The solution was dried and the oily residue was triturated with acetone-ether (4:1) solvent mixture to yield the solid product.

6.2. Attachment of Chelator to Antibody and Metal Ion

The specific monoclonal antibody utilized in the following experiments for injection into experimental animals was a rat IgG antibody specific for a Class I major histocompatability complex (MHC) antigen of Brown Norway (BN) rats. This antibody, designated CYT-015, was prepared by fusion of spleen cells from Lewis rats previously immunized by injection with cells from BN rats, with myeloma cell line SP2/0 AG14 according to the method described by McKearn, et al. (1979, Immunol. Rev. 47: 91–115). After cloning, CYT-015-containing ascites were generated by intraperitoneal injection of cells into pristane-primed nude mice. IgG monoclonal antibody was purified from this ascites by specific elution on a Protein-A-Sepharose column (Pharmacia Fine Chemicals, Piscataway, NJ).

A mouse monoclonal IgG antibody specific for a monomorphic determinant of a human Class I major histocompability complex was used as a carrier antibody for conjugates injected into control animals. This antibody is designated CYT-012.

6.2.1. Formation of Antibody-Chelator Conjugates

Radiolabeled antibody-metal ion complexes were prepared according to one method of the instant invention by first forming antibody-chelator conjugates. The carbohydrate moiety of the antibody (CYT-012 or CYT-015) was oxidized by reacting approximately 1 mg/ml glycoprotein in phosphate buffered saline (PBS) with 10 mM sodium metaperiodate ($NaIO_4$) (pH 6.0) for 1 hour on ice in the dark. The sample was then passed through a Sephadex G-25 column (Pharmacia Fine Chemicals, Piscataway, NJ) and the protein fractions pooled. The oxidized antibody was then attached to a compatible chelator and either used immediately or stored frozen at −20° C.

For example, glycyl-tyrosyl-lysine-diethylenetriaminepentaacetic acid (GYK-DTPA) was coupled to oxidized antibody by incubating an aliquot of the antibody with a 200-fold molar excess of GYK-DTPA in PBS (pH 6.0) for 30 minutes at room temperature. To stabilize the product sodium cyanoborohydride ($NaCNBH_3$) was added to a final concentration of 10 mM, and the reaction mixture was maintained at room temperature for a period ranging from 2 hours to overnight. The sample was then passed through a Sephadex® G-50 column (Pharmacia Fine Chemicals, Piscataway, NJ) and the protein fractions were pooled.

In other experiments, oxidized antibody was coupled either to p-aminoanilinediethylenetriaminepentaacetic acid (ADTPA) or polyethyleneimine-diethyenetriaminepentaacetic acid (PEI-DTPA) by the same method except that a 2000-fold molar excess of ADTPA or PEI-DTPA was utilized.

6.2.2. Formation of Antibody-Metal Ion Complexes

Radioactive metal ion was then attached to the antibody-chelator conjugates in order to form radioactive antibody-metal ion complexes useful for imaging systems.

For example, 20 /μl of stock $^{111}$Indium chloride ($^{111}$In-Cl$_3$) (New England Nuclear, Boston, MA) representing 1–2 mCi was added to 20 μl 0.5 M sodium acetate (pH 6.0), and incubated with antibody-chelator conjugate prepared as described above (50–200 μg) for 1 hour at 37° C. The sample was then eluted through a Sephadex G-50 column (Pharmacia Fine Chemicals, Piscataway, NJ) and the protein fractions pooled. The pooled $^{111}$In-labeled antibody-metal ion complex was rechromatographed through a Waters Protein Pak 300 sw high performance liquid chromatography (HPLC) column (Waters Associates, Milford, MA), and fractions were collected. The fraction corresponding to the elution volume of IgG in molecular weight represents the antibody-metal ion complex.

FIG. 1, for example, illustrates an HPLC chromatogram obtained during purification and isolation of $^{111}$Indium-labeled anti-Brown Norway major histocompatibility complex antibody-metal ion complex, $^{111}$In-CYT-015-ADTPA As shown in FIG. 1, the optical density of the fraction containing peak radioactivity reveals the similarity of the antibody-metal ion complex to monomeric unconjugated IgG.

7. EXAMPLES

Preparation of Antibody-Metal Ion Complexes via Carbohydrate or Sulfhydryl attachments The following examples illustrate the formation of compatible chelators and radiolabeled antibody-metal ion complexes prepared according to the instant invention.

7.1. Hydrazide-Ficoll

Ficoll 70 was obtained from Pharmacia Fine Chemicals, Inc. (Piscataway, N.J.). The carboxymethyl derivative of Ficoll 70 (CM-Ficoll) was prepared exactly as described by Inman (1975, J. Immunol. 114: 704). Two grams of CM-Ficoll were dissolved in 100 ml of water and 10 g of adipic dihydrazide were added slowly. The pH wa ad usted to 4.7 by the dropwise addition of 1 N HCl and then 1.25 g of 1-ethyl-3-(3-dimethylaminopropyl)carbodiimide were added and the pH was readjusted to 4.7 with 1 N HCl. The reaction mixture was then stirred for 20 hours at 23°-25° C. The crude reaction product was purified by gel filtration chromatography on a 4.5×55 cm column of Sephadex G-25. The column was eluted with phosphate buffered saline (PBS, 0.01 M sodium phosphate, 0.15 M sodium chloride, pH 7.4) and the void volume fractions were saved. The hydrazide-Ficoll was then dialyzed against water and lyophilized. The final product contained about 150 moles of hydrazide/mole of Ficoll.

7.2. (4-Iodoacetyl)-Aminobenzoichydrazide-Ficoll

Thirty milligrams of N-succinimidyl-(4-iodoacetyl)-aminobenzoate (SIAB, Pierce Chemical Co., Rockford, IL) were dissolved in 3 ml of acetonitrile. Six 0.48 ml aliquots of the SIAB solution were added to 20 ml of a 5 mg/ml solution of hydrazide-Ficoll (prepared as described in Section 7.1) dissolved in 0.1 M sodium phosphate buffer, pH 7.0, at 30 minute intervals. Before the second addition of SIAB solution, 5 ml of tetrahydrofuran were added to the hydrazide-Ficoll to clarify the solution. The reaction mixture was then stirred for 20 hours at 23°-25° C. The organic solvents were removed by bubbling $N_2$ gas through the reaction mixture and the resultant cloudy solution was clarified by centrifugation. The clear supernatant was lyophilized. Excess SIAB was removed by extracting the dry powder with tetrahydrofuran and the excess solvent was removed by evaporation under reduced pressure. The dry powder was dissolved in 5 ml of water and dialyzed for 4 hours at 4° C. The (4-iodoacetyl)-aminobenzoichydrazide-Ficoll was stored frozen at −70° C. and contained about 16 iodoacetyl groups per mole of hydrazide-Ficoll.

7.3. 2-Pyridyl Disulfide Hydrazide DTPA

Ten milligrams of hydrazide-DTPA (prepared as described in Section 6.1.4) were dissolved in 0.1 ml of 0.2 M sodium bicarbonate buffer, pH 9.5. One-tenth milliliter of 0.1 M sodium phosphate buffer, pH 7.2, was added and the pH of the resultant solution was adjusted to 8.0; 0.3 ml of tetrahydrofuran and 0.1 ml of N,N-dimethylformamide were then added. One hundred milligrams of N-succinimdyl-3-(2-pyridyl-dithio)propionate (Pharmacia Fine Chemicals, Inc., Piscataway, N.J.) dissolved in 1.0 ml of tetrahydrofuran were added to the hydrazide-DTPA solution and the reaction mixture was stirred for 16 hours at 23°-25° C. The tetrahydrofuran was removed by bubbling $N_2$ through the solution and the resultant suspension clarified by centrifugation. Unwanted reaction products were precipitated by the addition of 1 ml of water, and the clear supernatant was further purified by repeated gel filtration on columns of Bio-Gel P-2 (BioRad Laboratories, Richmond, Calif.) and eluted with water. The product contained about 0.15-0.20 moles of 2-pyridyl disulfide/mole of DTPA.

7.4. 3-Mercaptopropionichydrazide-DTPA-$^{153}$Gd

One milligram of 2-pyridyl disulfide hydrazide DTPA (PDS-DTPA, prepared as described in Section 7.3), was dissolved in 0.1 ml of water and labelled with 0.024 mCi of $^{153}$GdCl$_3$ (Amersham Corporation, Arlington Heights, Ill.) dissolved in 0.1 ml of 0.05 M HCl. The PDS-DTPA-$^{153}$Gd was then reduced with 5 mM dithiothreitol and the resultant 3-mercoptopropionichydrazide-DTPA-$^{153}$Gd was purified by gel filtration on Sephadex G-10.

7.5. $^{153}$Gd-DTPA-Hydrazide-Thioacetyl-Aminobenzoichydrazide Ficoll-Acetylthio-IgG One milligram of mouse anti-*N. gonorrhoeae* monoclonal IgG was diluted into 0.25 ml of PBS, pH 7.4. The IgG solution was then reduced with 5 mM dithiothreitol for 30 minutes at 23°-25° C. The reduced antibody was then passed over a 1×19 cm Sephadex G-50 column and eluted with 0.1 M tris(hydroxymethyl)-aminomethane buffer, pH 8.0, containing 1 mM ethylenediaminetetracetic acid (Tris/EDTA). One milligram of (4-iodoacetyl)-amino-benzoic-hydrazide-Ficoll (prepared as described in Section 7.2) was added to the reduced antibody and the reaction mixture was incubated at 4° C. for 16 hours to form an iodoacetyl-aminobenzoichydrazide-Ficoll-acetylthio-IgG conjugate.

0.20 milligrams of 3-mercaptopropionichydrazide-DTPA-$^{153}$Gd (prepared as described in Section 7.4) were added to the iodoacetyl-aminobenzoichydrazide-Ficoll-acetylthio-IgG conjugate and the reaction mixture incubated at 4° C. for 16 hours. The $^{153}$Gd-DTPA-hydrazide-thioacety-aminobenzoichydrazide Ficoll-acetylthio-IgG complex was purified by immunoadsorbtion with a resin composed of sheep anti-mouse IgG antibody (Cooper Biomedical, Scientific Division, Malvern, PA) covalently coupled to cyanogen bromide activated Sehparose 4B (Sigma Chemical Co., St. Louis, MO). The bound complex was eluted with 0.1 M glycine buffer, pH 2.0 and desalted into Tris/EDTA buffer using Sephadex G-25.

This is an example of the preparation of an antibody-metal ion complex formed by attachment of a single site compatible chelator at a plurality of sites introduced at the sulfhydryl groups of antibodies, as described in Section 5.2.

7.6. (4-Iodoacetyl)-Aminobenzoichydrazide-Ficoll-IgG

One-half milligram of mouse anti-*N. gonorrhoeae* monoclonal IgG was oxidized by the method of Section 6.2.1. After dialysis versus PBS, pH 7.4, the antibody was diluted with PBS, pH 7.4 to a final volume of 0.577 ml. 0.702 ml of (4-iodoacetyl)-aminobenzoichydrazide-Ficoll solution (16.7 mg/ml, prepared as described in Section 7.2), were added along with 0.128 ml of 110 mM sodium cyanoborohydride solution dissolved in 0.1 M sodium phosphate, pH 6.0. The reaction mixture was allowed to incubate for 2 hours at 23°–25° C. The (4-iodoacetyl)-aminobenzoichydrazide-Ficoll-IgG conjugate was purified by immunoadsorption with a resin composed of sheep anti-mouse IgG (Cooper Biomedical, Scientific Division, Malvern, PA) covalently coupled to cyanogen bromide activated Sepharose 4B (Sigma Chemical Co., St. Louis, MO). The bound conjugate was eluted with 0.1 M glycine buffer, pH 2.0 and desalted into 0.1 M Tris(hydroxymethyl)-aminomethane, pH 8.0, containing 1 mM ethylenediaminetetraacetic acid using Sephadex G-25. The purified conjugate contained about 2–30 moles of (4-iodoacetyl)-aminobenzoichydrazide-Ficoll/mole of IgG and was stored at −70° C.

7.7. $^{153}$Gd-DTPA-Hydrazide Thioacetyl-Aminobenzoichydrazide Ficoll-IgG 0.081 milligrams of 3-mercaptopropionic-hydrazide-DTPA-$^{153}$Gd (prepared as described in Section 7.4) were added to 0.050 mg of (4-iodoacetyl)-amino-benzoic-hydrazide-Ficoll-IgG prepared as described in section 7.6 and the reaction mixture was incubated overnight at 4° C. The free 3-mercaptopropionic hydrazide-DTPA-$^{153}$Gd was removed by chromatography on Sephadex G-50. The resultant $^{153}$Gd-DTPA-hydrazide thioacetyl aminobenzoichydrazide Ficoll-IgG complex contained 13.5 moles of DTPA/mole of IgG.

This is an example of the preparation of an antibody-metal ion complex formed by attachment of a single site compatible chelator at a plurality of sites introduced at the carbohydrate moieties of antibodies as described in Section 5.2.

7.8. Maleimide Hydrazide Ficoll

Twenty-two milligrams of 4-(N-maleimidomethyl)-cyclohexane-1-carboxylic acid N-hydroxysuccinimide ester (SMCC, Sigma Chemical Co., St. Louis, MO) were dissolved in 3 ml of tetrahydrofuran. Six 0.5 ml aliquots of the SMCC solution were added to 20 ml of a 5 mg/ml solution of hydrazide-Ficoll (prepared as described in Section 7.1), dissolved in 0.1 M sodium phosphate buffer, pH 6.8, at 30 minute intervals. Two milliliters of tetrahydrofuran were added to the reaction mixture before the second and third additions of SMCC solution. The organic solvents were then removed by bubbling $N_2$ through the reaction mixture and the resultant cloudy solution was clarified by centrifugation. The clear supernatant was lyophilized and the excess SMCC was extracted with tetrahydrofuran. The organic solvent was then removed by evaporation under reduced pressure. The final product contained about 15 moles of maleimide/mole of Ficoll. This compound can be used in the same way as the (4-iodoacetyl)-aminobenzoichydrazide-Ficoll prepared by the method of Section 7.2.

8. EXAMPLES

Imaging Using Radiolabeled Antibody-Metal ion complexes

The following examples illustrate methods for in vivo imaging to locate specific tissue or organ components utilizing the radiolabeled antibody-metal ion complexes prepared according to the instant invention.

8.1. Tumor Imaging

In one series of experiments, radiolabeled antibody-metal ion complexes were utilized to specifically locate tumorous tissues in experimental animals using a radioimaging system.

Nude mice were injected subcutaneously in the left hindquarter with $1 \times 10^6$ BN rat lymphoma cells. Seven days post-injection when tumor sizes ranged from 2–4 mm in diameter, the animals received a retro-orbital sinus or intravenous injection of 10 ug $^{111}$Indium-labeled anti-BN major histocompatability complex (MHC) antibody-metal ion complex, $^{111}$In-CYT-015-ADTPA. No animal received more than a single injection with complex.

Two groups of animals served as controls. One control group of non-tumor-bearing nude mice were injected either in the retro-orbital sinus or intravenously with 10 ug $^{111}$In-CYT-015-ADTPA. Another control group of nude mice bearing BN tumors were injected with 10 ug $^{111}$In-CYT-012-ADTPA.

Radioimaging was accomplished as follows: at 24, 48 or 72 hours post-injection with radiolabeled antibody-metal ion complex, animals were placed directly upon the inverted face of a gamma camera (General Electric Maxi Camera 37 interfaced with an ADEC Clinical Data System) Ten thousand–25,000 counts were routinely accumulated on exposed X-ray film without correction for background radiation.

Figure 2:
Figure 2:
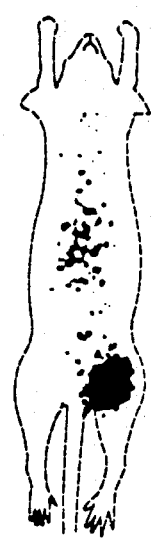
Figure 2:
Figure 2:
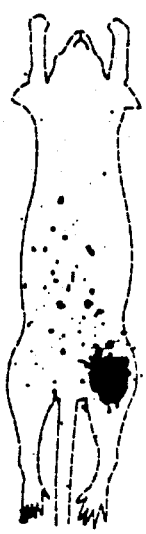

FIG. 2 illustrates in vivo images of radioactivity accumulated within BN tumor-bearing nude mice injected with $^{111}$In-CYT-015-ADTPA. Images A, B, C and were taken 24, 24, 48 and 72 hours after injection, respectively. FIG. 2 clearly demonstrates that the complexes of the invention are specifically localized at the intended target with extremely low levels of nonspecific localization.

Figure 3:
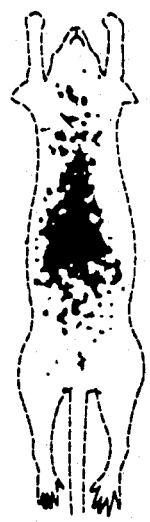
Figure 3:

FIG. 3 illustrates in vivo images of radioactivity in BN tumor-bearing control mice described above. Images E and F were taken 24 and 72 hours after injection, respectively. As shown, in FIG. 3 there was no detectable localization of radioactivity in BN tumor-bearing nude mice injected with $^{111}$In-CYT-012-ADTPA in which the antibody is specific for Class I human MHC antigen.

Figure 4:
FIG. 4 represents an autoradiographic image of control non-tumor-bearing nude mice injected with $^{111}$Indium-labeled anti-BN MHC antibody-metal ion complex, $^{111}$In-CYT-015-ADTPA. Images G and H were taken 24 and 72 hours after injection, respectively (see Section 8.1).
Figure 4:

FIG. 4. presents in vivo images of non-tumor-bearing nude mice injected with $^{111}$In-CYT-012-ADTPA Images G and H were taken 24 and 72 hours after injection, respectively. As shown in FIG. 4, there was also no detectable localization of radioactivity in non-tumor-bearing nude mice injected with radiolabeled antibody-metal ion complex, $^{111}$In-CYT-015-ADTPA, specific for BN tumor antigen.

8.2. Renal Transplant Imaging

In another series of experiments, radiolabeled antibody-metal ion complexes were utilized to specifically locate transplanted renal tissues by in vivo radioimaging.

Experimental rats bearing a transplanted functioning kidney or renal allograft were prepared as follows: the left kidney of a Lewis rat was surgically removed and a kidney from a BN×Lewis F1 rat was implanted in its place. The recipients' immune response against the foreign kidney transplant was chemically suppressed (see Stuart, et al., 1980, Immunol. Rev. 49: 127–165). Thus, the recipient rats possessed two functioning kidneys, only one of which carried the BN MHC antigen specifically recognized by CYT-015 antibody.

Figure 5:
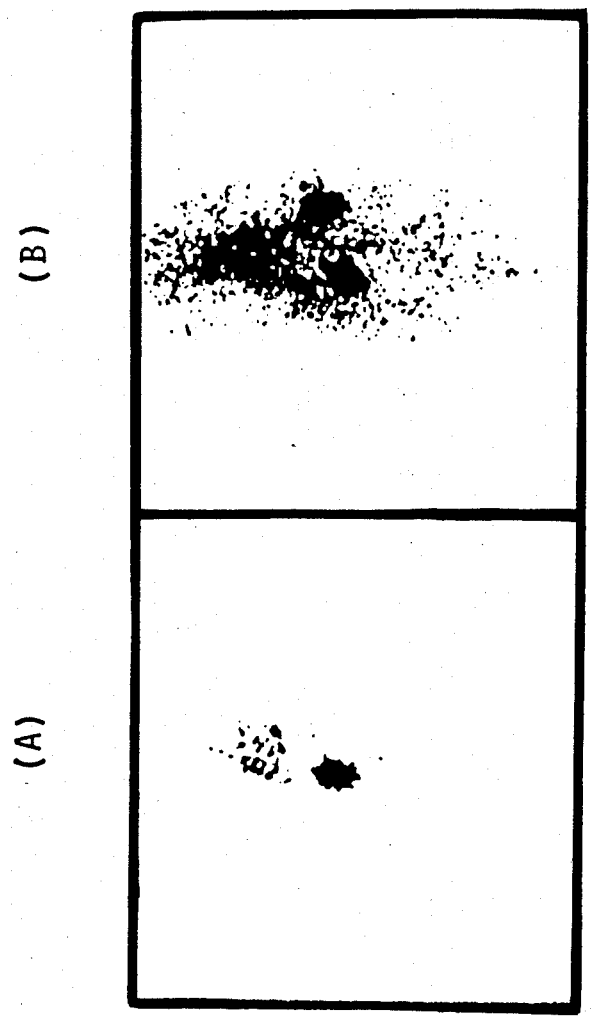
FIG. 5 represents an autoradiographic image of a Lewis rat with a transplanted BN X Lewis rat kidney injected with $^{111}$Indium-labeled anti-BN antibody-metal ion complex, $^{111}$In-CYT-015-ADTPA (image A) and then $^{99m}$Technetium-DTPA (image B, see Section 8.2).

Six to twelve months post-transplantation, the recipient rats were intravenously injected with 10 ug $^{111}$In-CYT-015-ADTPA, and imaged as described in Section 8.1 In FIG. 5, images A and B were taken approximately 1 hour and 20 minutes after intravenous injection.

As shown in FIG. 5, image A, the radionuclide localized within the transplanted kidney within approximately 1 hour and 20 minutes after intravenous injection of the labeled antibody-metal ion complex. Minimal accumulation of radioactivity was detected in the animal's kidney, lungs, spleen or liver.

FIG. 5, image B, illustrates the image obtained when the same recipient animal was injected with a commercially available renal imaging agent, $^{99m}$Technetium-DTPA chelate (Mallinkrodt, St. Louis, Mo.). Clearly, images obtained with $^{99m}$Technetium-DTPA chelate are inferior to those obtained with the antibody-metal ion complexes of the invention.

Both kidneys of the recipient animal were clearly functioning.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

We claim:

1. A method for preparing an antibody-chelator conjugate, comprising:
   (a) reacting an antibody or antibody fragment with an oxidizing agent to form an aldehyde group in the carbohydrate moiety of the antibody or antibody fragment, in which the carbohydrate moiety is not part of nor directly involved with the antigen binding site of the antibody or antibody fragment; and
   (b) reacting the aldehyde group of the resultant oxidized antibody or antibody fragment with a compatible chelator containing an amine group selected from the group consisting of primary amine, hydrazine, hydrazide, hydroxylamine, phenylhydrazine, semicarbazide and thiosemicarbazide groups to form a water-soluble antibody-chelator conjugate being characterized by (i) substantially the same immunospecificity as the unconjugated antibody or antibody fragment; and (ii) aqueous solubility such that the antibody-chelator conjugate, when reacted with a metal ion, is suitable for in vivo administration.

2. The method according to claim 1, wherein the oxidizing agent is an enzyme.

3. The method according to claim 1, wherein the oxidizing agent is an oxygen acid.

4. The method according to claim 1, wherein the antibody fragment is selected from the group consisting of Fab fragments, (Fab')$_2$ fragments and half antibody molecules.

5. The method according to claim 1, wherein the antibody or antibody fragment is a monoclonal antibody or a monoclonal antibody fragment.

6. The method according to claim 1, wherein the compatible chelator is an amine-containing derivative of diethylenetriaminepentaacetic acid.

7. The method according to claim 1, wherein the compatible chelator is selected from the group consisting of p-aminoaniline-diethylenetriaminepentaacetic acid, hydrazide-diethylenetriaminepentaacetic acid, phenylhydrazide-diethylenetriaminepentaacetic acid, hydroxylamine-diethylenetriaminepentaacetic acid, semicarbazide-diethylenetriaminepentaacetic acid, thiosemicarbazide-diethylenetriaminepentaacetic acid, polyethyleneimine-diethylenetriaminepentaacetic acid, p-phenylenediamine-diethylenetriaminepentaacetic acid, α-N-diethylenetriaminepentaacetic acid-L-lysine, glycyl-tyrosyl-lysine-diethylenetriaminepentaacetic acid, diethylenetriaminepentaacetic acid mono[(4-aminophenyl)methyl] amide and L-lysine benzyl ester-diethylenetriaminepentaacetic acid.

8. The method according to claim 1, wherein the compatible chelator is an amine-containing derivative of a chelator selected from the group consisting of ethylenediaminetetraacetic acid, dimercaptosuccinic acid, 2,3-dimercaptopropanesulfonic acid and metallothioein.

9. The method according to claim 1, wherein thee compatible chelator is an amine-containing derivative of a cryptate.

10. The method according to claim 1, wherein the antibody-chelator conjugate is stabilized by exposure to an effective amount of a reducing agent.

11. A method for preparing an antibody-metal ion complex, comprising:
    (a) reacting an antibody or antibody fragment with an oxidizing agent to form an aldehyde group in the carbohydrate moiety of the antibody or antibody fragment, in which the carbohydrate moiety is not part of nor directly involved with the antigen binding site of the antibody or antibody fragment;
    (b) reacting the aldehyde group of the resultant oxidized antibody or antibody fragment with a compatible chelator containing an amine group selected from the group consisting of primary amine, hydrazine, hydrazide, hydroxylamine, phenylhydrazine, semicarbazide and thiosemicarbazide groups to form a water-soluble antibody-chelator conjugate; and
    (c) combining the antibody-chelator conjugate with a metal ion under conditions which allow chelation of the metal ion to the antibody-chelator conjugate to form a water-soluble antibody-metal ion complex being characterized by (i) substantially the same immunospecificity as the unconjugated antibody or antibody fragment and (ii) an aqueous solubility such that the antibody metal ion complex is suitable for in vivo administration.

12. The method according to claim 11, wherein the metal ion is a radioisotope.

13. The method according to claim 12, wherein the radioisotope emits data particles.

14. The method according to claim 13, wherein the radioisotope is selected from the group consisting of $^{46}$Scandium, $^{47}$Scandium, $^{48}$Scandium, $^{72}$Gallium and $^{73}$Gallium.

15. The method according to claim 2, wherein the radioisotope emits alpha particles.

16. The method according to claim 15, wherein the radioisotope is selected from the group consisting of $^{211}$Bismuth, $^{212}$Bismuth, $^{213}$Bismuth and $^{214}$Bismuth.

17. The method according to claim 12, wherein the radioisotope emits positron particles.

18. The method according to claim 17, wherein the radioisotope is selected from the group consisting of $^{43}$Scandium, $^{44}$Scandium, $^{52}$Iron, $^{55}$Cobalt and $^{68}$Gallium.

19. The method according to claim 11, wherein the metal ion is paramagnetic.

20. The method according to claim 19, wherein the metal ion is selected from the group consisting of $^{54}$Iron, $^{56}$Iron, $^{57}$Iron, $^{58}$Iron, $^{157}$Gadolinium and $^{55}$Manganese.

21. The method according to claim 11, wherein the oxidizing agent is an enzyme.

22. The method according to claim 11, wherein the oxidizing agent is an oxygen acid.

23. The method according to claim 11, wherein the antibody fragment is selected from the group consisting of Fab fragments, (Fab')$_2$ fragments and half antibody molecules.

24. The method according to claim 11, wherein the antibody or antibody fragment is a monoclonal antibody or monoclonal antibody fragment.

25. The method according to claim 11, wherein the compatible chelator is an amine-containing derivative of diethylenetriaminepentaacetic acid.

26. The method according to claim 11, wherein the compatible chelator is selected from the group consisting of p-aminoaniline-diethylenetriaminepentaacetic acid, hydrazide-diethylenetriaminepentaacetic acid, phenylhydrazide-diethylenetriaminepentaacetic acid, hydroxylamine-diethylenetriaminepentaacetic acid, semicarbazide-diethylenetriaminepentaacetic acid, thiosemicarbazide-diethylenetriaminepentaacetic acid, polyethyleneimine-diethylenetriaminepentaacetic acid, p-phenylenediamine-diethylenetriaminepentaacetic acid, α-N-diethylentriminepentacetic acid L-lysine, glycyl-tyrosyl-lysinediethylentriaminepentaacetic acid, diethylenetriaminepentaacetic acid mono [(4-aminophenyl)methyl]amide and L-lysine benzyl ester-diethylenetriaminepentaacetic acid.

27. The method according to claim 11, wherein the compatible chelator is an amine-containing derivative of a chelator selected from the group consisting of ethylenediaminetetraacetic acid, dimercaptosuccinic acid, 2,3-dimercaptopropanesulfonic acid and metallothioein.

28. The method according to claim 11, wherein the compatible chelator is an amine-containing derivative of a cryptate.

29. The method according to claim 11, wherein the antibody-metal ion complex is stabilized by exposure to an effective amount of a reducing agent.

30. The method according to claim 11, further comprising the step of:
(d) separating the antibody-metal ion complexes from non-chelated metal ions to obtain antibody-metal ion complexes substantially free of non-chelated metal ions.

31. The method according to claim 30, wherein the separation is accomplished by high performance gel permeation liquid chromatography.

32. A method for preparing an antibody-metal ion complex, comprising:
(a) reacting an antibody or antibody fragment with an oxidizing agent to form an aldehyde group in the carbohydrate moiety of the antibody or antibody fragment, in which the carbohydrate moiety is not part of nor directly involved with the antigen binding site of the antibody or antibody fragment; and
(b) reacting the aldehyde group of the resultant oxidized antibody or antibody fragment with a chelator-metal ion complex, said chelator-metal ion complex comprising a compatible chelator-metal ion complex comprising a compatible chelator containing an amine group selected from the group consisting of primary amine, hydrazine, hydrazide, hydroxylamine, phenylhydrazine, semicarbazide and thiosemicarbazide groups coordinately bound to a metal ion, to form a water-soluble antibody-metal ion complex being characterized by (i) substantially the same immunospecificity as the unconjugated antibody or antibody fragment, and (ii) aqueous solubility such that the antibody-chelator metal ion complex is suitable for in vivo administration.

33. The method according to claim 32, wherein the metal ion is a radioisotope.

34. The method according to claim 33, wherein the radioisotope emits beta particles.

35. The method according to claim 34, wherein the radioisotope is selected from the group consisting of $^{46}$Scandium, $^{47}$Scandium, $^{48}$Scandium, $^{72}$Gallium and $^{73}$Gallium.

36. The method ccording to claim 33, wherein the radioisotope emits alpha particles.

37. The method according claim 36, wherein the radioisotope is selected from the group consisting of $^{211}$Bismuth, $^{212}$Bismuth, $^{213}$Bismuth and $^{214}$Bismuth.

38. The method according to claim 33, wherein the radioisotope emits positron particles.

39. The method according to claim 38, wherein the radioisotope is selected from the group consisting of $^{43}$Scandium, $^{44}$Scandium, $^{52}$Iron, $^{55}$Cobalt and $^{68}$Gallium.

40. The method according to claim 32, wherein the metal ion is paramagnetic.

41. The method according to claim 40, wherein the metal ion is selected from the group consisting of $^{54}$Iron, $^{56}$Iron, $^{57}$Iron, $^{58}$Iron, $^{157}$Gadolinium and $^{55}$Manganese.

42. The method according to claim 32, wherein the oxidizing agent is an enzyme.

43. The method according to claim 32, wherein the oxidizing agent is an oxygen acid.

44. The method according to claim 32, wherein the antibody fragment is selected from the group consisting of Fab fragments, (Fab')$_2$ fragments and half antibody molecules.

45. The method according to claim 32, wherein the antibody or antibody fragment is a monoclonal antibody or monoclonal antibody fragment.

46. The method according to claim 32, wherein the compatible chelator is an amine-containing derivative of diethylenetriaminepentaacetic acid.

47. The method according to claim 32, wherein the compatible chelator is selected from the group consisting of p-aminoaniline-diethylenetriaminepentaacetic acid, hydrazide-diethylenetriaminepentaacetic acid, phenylhydrazide-diethylenetriaminepentaacetic acid, hydroxylamine-diethylenetriaminepentaacetic acid, semicarbazide-diethylenetriaminepentaacetic acid, thiosemicarbazide-diethylenetriaminepentaacetic acid, polyethyleneimine-diethylenetriaminepentaacetic acid, p-phenylenediamine-diethylenetriaminepentaacetic acid, α-N-diethylenetriaminepentaacetic acid-L-lysine, glycyl-tyrosyl-lysine-diethylenetriaminepentaacetic acid, diethylenetriaminepentaacetic acid mono[(4-aminophenyl)methyl]amide and L-lysine benzyl ester-diethylenetriaminepentaacetic acid.

48. The method according to claim 32, wherein the compatible chelator is an amine-containing derivative of a chelator selected from the group consisting of ethylenediaminetetraacetic acid, dimercaptosuccinic acid, 2,3-dimercaptopropanesulfonic acid and metallothioein.

49. The method according to claim 32, wherein the compatible chelator is an amine-containing derivative of a cryptate.

50. The method according to claim 32, werein the antibody-metal ion complex is stabilized by exposure to an effective amount of a reducing agent.

51. The method according to claim 32, further comprising the step of:
(c) separating the antibody-metal ion complexes from non-chelated metal ions to obtain antibody-metal ion complexes substantially free of non-chelated metal ions.

52. The method according to claim 51, wherein the separation is accomplished by high performance gel permeation liquid chromatography.

53. An antibody-chelator conjugate, comprising: a compatible chelator attached through a covalent bond to a carbohydrate moiety of an oxidized antibody or antibody fragment, in which the carbohydrate moiety is not part or nor directly involved with the antigen binding site of the antibody or antibody fragment, said water-soluble antibody-chelator conjugate being characterized (i) substantially the same immunospecificity as the unconjugated antibody or antibody fragment, and (ii) aqueous solubility such that the antibody-chelator conjugate, when reacted with a metal ion, is suitable for in vivo administration.

54. The antibody-chelator conjugate according to claim 53, wherein the covalent bond is an enamine, hydrazone, oxime, phenylhydrazone, semicarbazone, thiosemicarbazone, or a reduced form thereof.

55. The antibody-chelator conjugate according to claim 53, wherein the antibody fragment is selected from the group consisting of Fab fragments, (Fab')$_2$ fragments and half antibody molecules.

56. The antibody-chelator conjugate according to claim 53, wherein the antibody or antibody fragment is a monoclonal antibody or monoclonal antibody fragment.

57. The antibody-chelator conjugate according to claim 53, wherein the compatible chelator is an amine-containing derivative of diethylenetriaminepentaacetic acid.

58. The antibody-chelator conjugate according to claim 57, wherein the compatible chelator is selected from the group consisting of p-aminoaniline-diethylenetriaminepentaacetic acid, hydrazide-diethylenetriaminepentaacetic acid, phenylhydrazide-diethylenetriaminepentaacetic acid, hydroxylamine-diethylenetriaminepentaacetic acid, semicarbazide-diethylenetriaminepentaacetic acid, thiosemicarbazide-diethylenetriaminepentaacetic acid, polyethyleneimine-diethylenetriaminetetraacetic acid p-phenylenediamine-diethylenetriaminepentaacetic acid, α-N-diethylenetriaminepentaacetic acid-L-lysine, glycyl-tyrosyl-lysine-diethylenetriaminepentaacetic acid, diethylenetriaminepentaacetic acid mono[((4-aminophenyl)methyl]amide and L-lysine benzyl ester-diethylenetriaminepentaacetic acid.

59. The antibody-chelator conjugate according to claim 53, wherein the compatible chelator is an amine-containing derivative of a chelator selected from the group consisting of ethylenediaminetetraacetic acid, dimercaptosuccinic acid, 2,3-dimercaptopropanesulfonic acid and metallothioein.

60. The antibody-chelator conjugate according to claim 53, wherein the compatible chelator is an amine-containing derivative of a cryptate.

61. An antibody-metal ion complex, comprising: an antibody-chelator conjugate comprising a compatible chelator attached through a covalent bond to a carbohydrate moiety of an oxidized antibody or antibody fragment, in which the carbohydrate moiety is not part of nor directly involved with the antigen binding site of the antibody or antibody fragment; said water-soluble antibody-chelator conjugate coordinately bound through said compatible chelator to a metal ion to form a water-soluble antibody-metal ion complex being characterized by (i) substantially the same immunospecificity as the unconjugated antibody or antibody fragment, and (ii) aqueous solubility such that the antibody-chelator metal ion complex is suitable for in vivo administration.

62. The antibody-metal ion complex according to claim 61, wherein the metal ion is a radioisotope.

63. The antibody-metal ion complex according to claim 62, wherein the radioisotope emits beta particles.

64. The antibody-metal ion complex according to claim 63, wherein the radioisotope is selected from the group consisting of $^{46}$Scandium, $^{47}$Scandium, $^{48}$Scandium, $^{72}$Gallium and $^{73}$Gallium.

65. The antibody-metal ion complex according to claim 62, wherein the radioisotope emits alpha particles.

66. The antibody-metal ion complex according to claim 65, wherein the radioisotope is selected from the group consisting of $^{211}$Bismuth, $^{212}$Bismuth, $^{213}$Bismuth $^{214}$Bismuth.

67. The antibody-metal ion complex according to claim 62, wherein the radioisotope emits positron particles.

68. The antibody-metal ion complex according to claim 67, wherein the radioisotope is selected from the group consisting of $^{43}$Scandium, $^{44}$Scandium, $^{52}$Iron, $^{55}$Cobalt and $^{68}$Gallium.

69. The antibody-metal ion complex according to claim 61, wherein the metal ion is paramagnetic.

70. The antibody-metal ion complex according to claim 69, wherein the metal ion is selected from the group consisting of $^{54}$Iron, $^{56}$Iron, $^{57}$Iron, $^{58}$Iron, $^{157}$Gadolinium and $^{55}$Manganese.

71. The antibody-metal ion complex according to claim 61, wherein the covalent bond is an imine, hydrazone, oxime, phenylhydrazone, semicarbazone, thiosemicarbazone or a reduced form thereof.

72. The antibody-metal ion complex according to claim 61, wherein the antibody fragment is selected from the group consisting of Fab fragments, (Fab')$_2$ fragments and half antibody molecules.

73. The antibody-metal ion complex according to claim 61, wherein the antibody or antibody fragment is a monoclonal antibody or monoclonal antibody fragment.

74. The antibody-metal ion complex according to claim 61, wherein the compatible chelator is an amine-containing derivative of diethylenetriaminepentaacetic acid.

75. The antibody-metal ion complex according to claim 61, wherein the compatible chelator is selected from the group consisting of p-aminoaniline-diethylenetriaminepentaacetic acid, hydrazide-diethylenetriaminepentaacetic acid, phenylhydrazide-diethylenetriaminepentaacetic acid, hydroxylamine-diethylenetriaminepentaacetic acid, semicarbazide-diethylenetriaminepentaacetic acid, thiosemicarbazide-diethylenetriaminepentaacetic acid, polyethyleneimine-diethylenetriaminepentaacetic acid, p-phenylenediamine-diethylenetriaminepentaacetic acid, α-N-diethylenetriaminepentaacetic acid-L-lysine, glycyl-tyrosyl-lysine-diethylenetriaminepentaacetic acid, diethylenetriaminepentaacetic acid mono[(4-aminophenyl)methyl]amide and L-lysine benzyl ester-diethylenetriaminepentaacetic acid.

76. The antibody-metal ion complex according to claim 61, wherein the compatible chelator is an amine-containing derivative of a chelator selected from the group consisting of ethylenediaminetetraacetic acid, dimercaptosuccinic acid, 2,3-dimercaptopropanesulfonic acid and metallothioein.

77. The antibody-metal ion complex according to claim 61, wherein the compatible chelator is an amine-containing derivative of a cryptate.

78. The antibody-metal ion complex according to claim 61, substantially free of non-chelated metal ions.

79. A method for in vivo imaging a specific tissue, comprising:
   (a) administering to an animal or a human an effective amount of a water-soluble antibody metal ion complex which
      (i) is immunoreactive with and immunospecific for an antigenic determinant of the specific tissue and substantially non-immunoreactive with and non-immunospecific for non-specific tissue and the antigenic determinant is not found in substantial amounts in non-specific tissue; and
      (ii) comprises an antibody or antibody fragment, a compatible chelator and metal ion in which the compatible chelator is covalently bound to the antibody or antibody fragment at a carbohydrate moiety located outside the antigen binding region of the antibody or antibody fragment, and coordinately bound to the metal ion so that the antibody-metal ion complex is characterized by substantially the same immunospecificity as the antibody or antibody fragment and an aqueous solubility such that the antibody-metal ion complex is suitable for administration in vivo; and
   (b) detecting whether the antibody-metal ion complex localized at the specific tissue.

80. A method for therapeutic treatment of a cellular disorder, comprising: administering to an animal or a human a therapeutically effective amount of a water-soluble antibody metal-ion complex which
   (a) is immunoreactive with and immunospecific for a target site associated with the cellular disorder and substantially non-immunoreactive with and non-immunospecific for tissue not associated with the cellular disorder; and
   (b) which comprises an antibody or antibody fragment, a compatible chelator and a metal ion which emits cytotoxic beta or alpha particles, in which the compatible chelator is covalently bound to the antibody or antibody fragment at a carbohydrate moiety located outside the antigen binding region of the antibody or antibody fragment, and coordinately bound to the metal ion so that the antibody-metal ion complex is characterized by substantially the same immunospecificity as the antibody or antibody fragment and an aqueous solubility such that the antibody-metal ion complex is suitable for administration in vivo.

81. A method for testing for an antigen, comprising:
   (a) mixing a sample suspected of containing the antigen with a water-soluble antibody metal ion complex which
      (i) is immunoreactive with and immunospecific for the antigen; and
      (ii) which comprises an antibody or antibody fragment, a compatible chelator and metal ion in which the compatible chelator is covalently bound to the antibody or antibody fragment at a carbohydrate moiety located outside the antigen binding region of the antibody or antibody fragment, and coordinately bound to the metal ion so that the antibody-metal ion complex is characterized by substantially the same immunospecificity as the antibody or antibody fragment and an aqueous solubility such that the antibody-metal ion complex is suitable for administration in vivo; and
   (b) detecting any interaction of the antibody-metal ion complex with the sample.

* * * * *